US012787945B2

(12) United States Patent
Oh et al.

(10) Patent No.: US 12,787,945 B2
(45) Date of Patent: Nov. 10, 2026

(54) LIGHT SOURCE MODULE FOR PLANT CULTIVATION AND LIGHT SOURCE DEVICE INCLUDING THE SAME

(71) Applicants: INDUSTRY-UNIVERSITY COOPERATION FOUNDATION OF CHUNGBUK NATIONAL UNIVERSITY, Chungcheongbuk-do (KR); SEOUL VIOSYS CO., LTD., Gyeonggi-do (KR)

(72) Inventors: Myung Min Oh, Gyeonggi-do (KR); Yoon Seon Choi, Gyeonggi-do (KR)

(73) Assignees: INDUSTRY-UNIVERSITY COOPERATION FOUNDATION OF CHUNGBUK NATIONAL UNIVERSITY; SEOUL VIOSYS CO., LTD.

( * ) Notice: Subject to any disclaimer, the term of this patent is extended or adjusted under 35 U.S.C. 154(b) by 139 days.

(21) Appl. No.: 18/124,549

(22) Filed: Mar. 21, 2023

(65) Prior Publication Data

US 2023/0247944 A1 Aug. 10, 2023

Related U.S. Application Data

(63) Continuation of application No. PCT/KR2021/012945, filed on Sep. 23, 2021.

(Continued)

(51) Int. Cl.

| | |
|---|---|
| ***A01G 7/04*** | (2006.01) |
| ***A01G 9/24*** | (2006.01) |
| ***A01H 1/00*** | (2006.01) |

(52) U.S. Cl.

CPC ............ *A01G 7/045* (2013.01); *A01G 9/249* (2019.05); *A01H 1/10* (2021.01)

(58) Field of Classification Search

CPC ................................ A01G 7/045; A01G 9/249

See application file for complete search history.

(56) References Cited

U.S. PATENT DOCUMENTS

| | | | | |
|---|---|---|---|---|
| 10,433,493 | B2 | 10/2019 | Barber, III et al. | |
| 2001/0047618 | A1 * | 12/2001 | Fang ..................... | A01G 9/249 47/65.5 |

(Continued)

FOREIGN PATENT DOCUMENTS

| | | | |
|---|---|---|---|
| EP | 3616499 | A1 | 3/2020 |
| JP | 2018186802 | A | 11/2018 |

(Continued)

OTHER PUBLICATIONS

Mahdavian, K. et al. The effects of ultraviolet radiation on the contents of chlorophyll, flavonoid, anthocyanin and proline in *Capsicum annuum* L.Turk J Bot. 2008, vol. 32, pp. 25-33.

(Continued)

*Primary Examiner* — Kristen C Hayes
(74) *Attorney, Agent, or Firm* — LaBatt, LLC

(57) ABSTRACT

A light source module for plant cultivation and a light source device including the same. The light source module changes a phytochemical content in a plant through UV treatment of the plant. The light source module may include: a first light source emitting a first type of light changing the content of at least one of multiple phytochemicals; and a second light source emitting a second type of light changing the content of at least one of the multiple phytochemicals. The at least one phytochemical changed in content by the first type of light may be a different kind of phytochemical from the at least one phytochemical changed in content by the second type of light. The first light source and the second light source may be individually operated. In addition, the first (Continued)

type of light and the second type of light may be UV light having different peak wavelengths.

32 Claims, 33 Drawing Sheets

Related U.S. Application Data

(60) Provisional application No. 63/082,111, filed on Sep. 23, 2020.

(56) References Cited

U.S. PATENT DOCUMENTS

| | | | | |
|---|---|---|---|---|
| 2008/0298052 | A1* | 12/2008 | Hurst | A01G 7/045 362/231 |
| 2012/0075848 | A1* | 3/2012 | Yamada | A01G 9/249 362/231 |
| 2019/0098842 | A1* | 4/2019 | Barber, III | A01G 9/246 |
| 2019/0150378 | A1 | 5/2019 | Oh et al. | |
| 2020/0060099 | A1* | 2/2020 | Kim | A01G 7/045 |
| 2020/0120878 | A1 | 4/2020 | Ko et al. | |
| 2020/0178474 | A1 | 6/2020 | Oh et al. | |
| 2021/0112726 | A1 | 4/2021 | Okazawa et al. | |
| 2021/0204485 | A1* | 7/2021 | Oh | H01L 25/0753 |
| 2021/0307254 | A1* | 10/2021 | Oh | A01G 7/045 |

FOREIGN PATENT DOCUMENTS

| | | | |
|---|---|---|---|
| KR | 1020180006325 | A | 1/2018 |
| KR | 1020180119383 | A | 11/2018 |
| WO | 2020040598 | A1 | 2/2020 |

OTHER PUBLICATIONS

English translation of International Search Report for PCT/KR2021/012945, Jan. 19, 2022, 2 pages.

Extended European Search Report for European Patent Application No. 21872899.6, Sep. 6, 2024, 9 pages.

* cited by examiner

LIGHT SOURCE MODULE FOR PLANT CULTIVATION AND LIGHT SOURCE DEVICE INCLUDING THE SAME

CROSS-REFERENCE TO RELATED APPLICATIONS AND PRIORITY

The present application is a continuation application of International Application No. PCT/KR2021/012945, filed Sep. 23, 2021, which claims priority to and the benefit of U.S. Provisional Application No. 63/082,111, filed on Sep. 23, 2020, each of which is incorporated by reference for all purposes as if fully set forth herein.

TECHNICAL FIELD

Embodiments of the present disclosure relate to a light source module for plant cultivation and a light source device including the same.

BACKGROUND ART

As a luminaire for plant cultivation, various light sources have been developed and used to replace sunlight. Conventionally, incandescent lamps and fluorescent lamps have been mainly used as luminaires for plant cultivation. However, most typical luminaires for plant cultivation only provide light having a specific wavelength suitable for photosynthesis of plants and do not have any additional functions.

Plants can synthesize phytochemicals useful to humans through resistance to various stresses. Therefore, there is a need for a light source and a cultivation method that can cultivate plants containing a high content of the phytochemicals useful to humans.

SUMMARY

Technical Problem

Embodiments of the present disclosure provide a light source for plant cultivation, which can increase a phytochemical content in a plant, and a light source device including the same.

Technical Solution

In accordance with one embodiment of the present disclosure, there is provided a light source module for plant cultivation, which can change a phytochemical content in a plant through UV treatment of the plant.

The light source module may include: a first light source emitting a first type of light changing the content of at least one of multiple phytochemicals; and a second light source emitting a second type of light changing the content of at least one of the multiple phytochemicals.

The at least one of the multiple phytochemicals changed in content by the first type of light may be a different kind of phytochemical from the at least one of the multiple phytochemicals changed in content by the second type of light.

The first light source and the second light source may be individually operated.

The first type of light and the second type of light may be ultraviolet (UV) light having different peak wavelengths.

In accordance with another embodiment of the present disclosure, there is provided a light source device for plant cultivation, which includes a light source module, an input unit, a setting unit, and a controller.

The light source module may perform UV treatment on a plant by irradiating the plant with UV light. The input unit may receive an external signal. The setting unit may set a UV treatment in response to the external signal from the input unit. The controller may control operation of the light source module in response to a signal from the input unit or the setting unit.

The light source module may include: a first light source emitting a first type of light changing the content of at least one of multiple phytochemicals; and a second light source emitting a second type of light changing the content of at least one of the multiple phytochemicals.

The at least one of the multiple phytochemicals changed in content by the first type of light may be a different kind of phytochemical from the at least one of the multiple phytochemicals changed in content by the second type of light.

The first light source and the second light source may be individually operated.

The first type of light and the second type of light may be UV light having different peak wavelengths.

ADVANTAGEOUS EFFECTS

The light source module for plant cultivation and the light source device for plant cultivation can selectively increase the content of a particular phytochemical among multiple phytochemicals in a plant. That is, the light source module and the light source device can selectively increase the content of phytochemicals having a certain efficacy.

DETAILED DESCRIPTION

Figure 1:
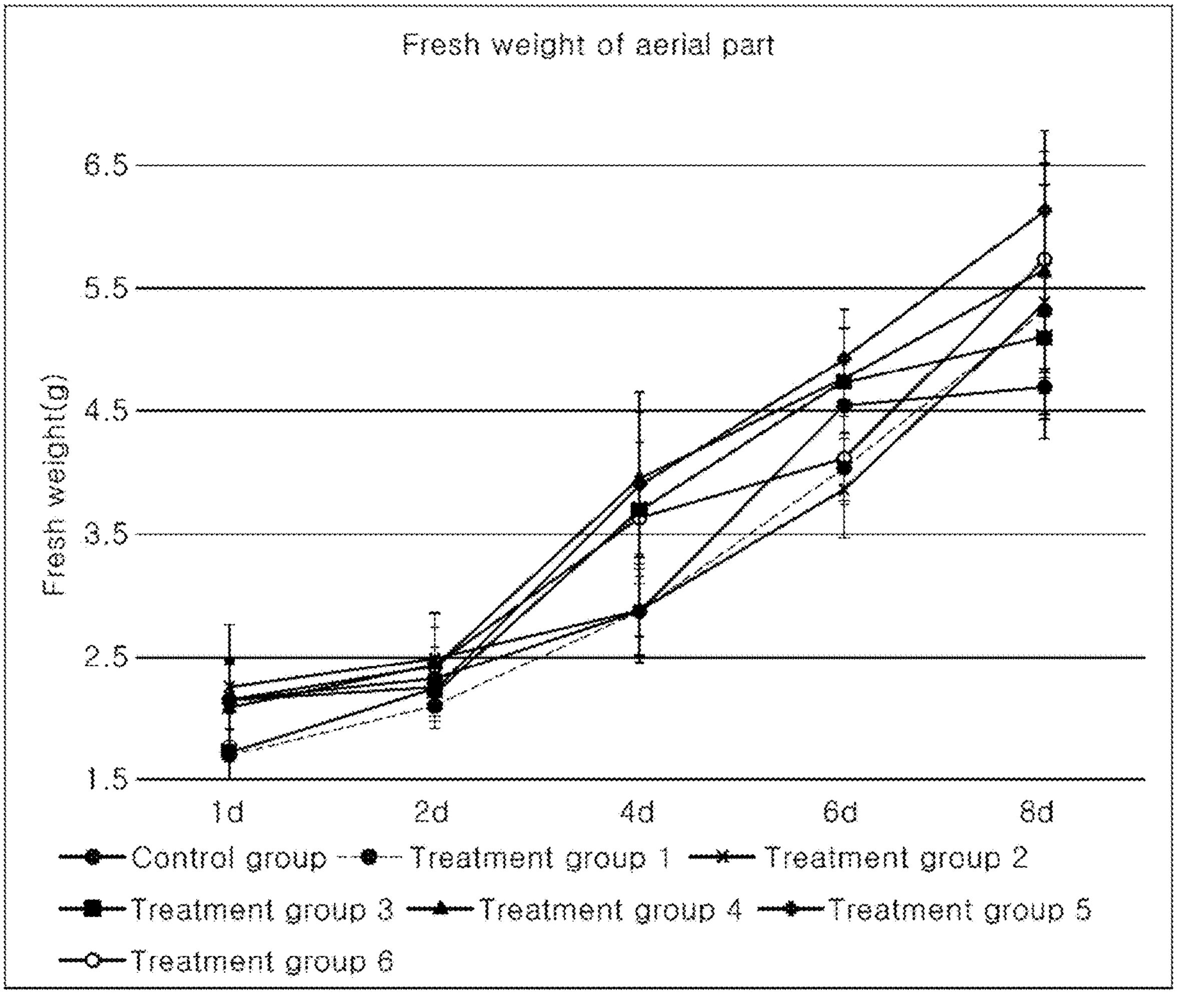
FIG. 1 is a graph depicting fresh weights of an aerial part of a plant according to UV treatment conditions.

Hereinafter, embodiments of the present disclosure will be described with reference to the accompanying drawings. It should be understood that the embodiments are provided for complete disclosure and thorough understanding of the present disclosure by those skilled in the art. Therefore, the present disclosure is not limited to the following embodiments and may be embodied in different ways. In addition, the drawings may be exaggerated in width, length, and thickness of components for descriptive convenience and clarity only. Like components will be denoted by like reference numerals throughout the specification.

According to one embodiment, a light source module for plant cultivation may change a phytochemical content in a plant through UV treatment of the plant.

The light source module may include: a first light source emitting a first type of light changing the content of at least one of multiple phytochemicals; and a second light source emitting a second type of light changing the content of at least one of the multiple phytochemicals.

The at least one of the multiple phytochemicals changed in content by the first type of light may be a different kind of phytochemical from the at least one of the multiple phytochemicals changed in content by the second type of light.

The first light source and the second light source may be individually operated.

The first type of light and the second type of light may be ultraviolet (UV) light having different peak wavelengths.

At least one of the first type of light and the second type of light may be UVB.

For example, the first type of light may be UVB and the second type of light may be UVA.

The light source module may increase the content of at least one of hydroxycinnamic acid, flavonoids and anthocyanin in the plant through UV treatment.

The first type of light may be UV light having a peak wavelength of 295 nm.

The first type of light may have an irradiance of 0.1 $W/m^2$ or 0.3 $W/m^2$.

The first light source may emit the first type of light for 6 hours in a daily photoperiod.

The first light source may continuously emit the first type of light.

The first light source may repeat emission of the first type of light and stopping emission of the first type of light.

The first type of light may increase the content of at least one of hydroxycinnamic acid, anthocyanin, and flavonoid-based quercetin-3-O-malonyl glucoside and luteolin hydroxymalonyl hexoside.

The second type of light may be UV light having a peak wavelength of 385 nm.

The second type of light may have an irradiance of 30 $W/m^2$.

The second light source may continuously emit the second type of light for a period of UV treatment.

The second type of light may increase the content of at least one of hydroxycinnamic acid-based caffeoyltartaric acid, and flavonoid-based quercetin-3-O-(6"-O-malonyl)-glucoside-7-O-glucoside and kaempferol malonyl glucoside.

The period of UV treatment may be 4 to 8 days.

In accordance with another embodiment, a light source device for plant cultivation may include a light source module, an input unit, a setting unit, and a controller.

The light source module may perform UV treatment on a plant by irradiating the plant with UV light. The input unit may receive an external signal. The setting unit may set a UV treatment method in response to the external signal from the input unit. The controller may control operation of the light source module in response to a signal from the input unit or the setting unit.

The light source module may include: a first light source emitting a first type of light changing the content of at least one of multiple phytochemicals; and a second light source emitting a second type of light changing the content of at least one of the multiple phytochemicals.

The at least one of the multiple phytochemicals changed in content by the first type of light may be a different kind of phytochemical from the at least one of the multiple phytochemicals changed in content by the second type of light.

The first light source and the second light source may be individually operated.

The first type of light and the second type of light may be UV light having different peak wavelengths.

At least one of the first type of light and the second type of light may be UVB.

For example, the first type of light may be UVB and the second type of light may be UVA.

The light source module may increase the content of at least one of hydroxycinnamic acid, flavonoids and anthocyanin in the plant through UV treatment.

The first type of light may be UV light having a peak wavelength of 295 nm.

The controller may control the first light source to emit the first type of light at an irradiance of 0.1 $W/m^2$ or 0.3 $W/m^2$.

The controller may control the first light source to emit the first type of light for 6 hours in a daily photoperiod.

The controller may control the first light source to continuously emit the first type of light.

The controller may control the first light source to repeat emission of the first type of light and stopping emission of the first type of light.

The first type of light may increase the content of at least one of hydroxycinnamic acid, anthocyanin, and flavonoid-based quercetin-3-O-malonyl glucoside and luteolin hydroxy malonyl hexoside.

The second type of light may be UV light having a peak wavelength of 385 nm.

The controller may control the second light source to emit the second type of light at an irradiance of 30 $W/m^2$.

The controller may control the second light source to continuously emit the second type of light for a period of UV treatment.

The second type of light may increase the content of at least one of hydroxycinnamic acid-based caffeoyltartaric acid, and flavonoid-based quercetin-3-O-(6"-O-malonyl)-glucoside-7-O-glucoside and kaempferol malonyl glucoside.

The period of UV treatment may be 4 to 8 days.

The external signal may include one selected from among the kind of phytochemical, the type of light, light intensity, a light treatment time, and an irradiation method.

The setting unit may set a UV treatment method depending upon the kind of phytochemical selected on the input unit.

The controller may control the light source module in response to a signal including data of the UV treatment method received from the setting unit.

The UV treatment method may include at least one of the type of light, the light intensity, the light treatment time, and the irradiation method.

Next, embodiments of the present disclosure will be described in detail with reference to the accompanying drawings.

Embodiments of the present disclosure relate to a light source module for plant cultivation, which can increase a phytochemical content in a plant, and a light source device including the same.

First, an experiment was performed to check reaction of a plant depending upon UV treatment conditions.

The plant used in the experiment was red leaf lettuce.

For experiment, the red leaf lettuce was sown in a seed growing pack and grown into seedlings for 2 weeks, which were in turn transplanted into a deep-flow technique (DFT) system, followed by cultivation for 3 weeks. Cultivation was carried out in the DFT system under conditions of a temperature of 20° C., a humidity of 60%, and a photoperiod of 12 hours. A light source used for cultivation was a visible LED (red light:white light=9:1) and had a photon flux density of 150 $\mu$mol/cm$^2$/s.

UV Treatment on red leaf lettuce samples was started using LEDs 3 weeks after transplantation of the red leaf lettuce samples in the DFT system. UV Treatment was performed using a UVA LED and a UVB LED.

Treatment group 1, Treatment group 2, Treatment group 3, Treatment group 4 and Treatment group 6 were groups of red leaf lettuce samples irradiated with UVB, and Treatment group 5 was a group of red leaf lettuce samples irradiated with UVA. UVA was continuously emitted to the red leaf lettuce samples for 8 days and UVB was emitted to the red leaf lettuce samples for 6 hours in every daily photoperiod for 8 days.

More specifically, Treatment group 1 is a group of red leaf lettuce samples continuously irradiated with UV light having a peak wavelength of 295 nm at an irradiance of 0.1 W/m$^2$ for 6 hours in every daily photoperiod for 8 days. For 8 days of UV treatment, Treatment group 1 was irradiated with a total UV dose of about 17.28 kJ/m$^2$ for 8 days.

Treatment group 2 is a group of red leaf lettuce samples continuously irradiated with UV light having a peak wavelength of 295 nm at an irradiance of 0.3 W/m$^2$ for 6 hours in every daily photoperiod for 8 days. For 8 days of UV treatment, Treatment group 2 was irradiated with a total UV dose of about 51.84 kJ/m$^2$ for 8 days.

Treatment group 3 is a group of red leaf lettuce samples irradiated with UV light having a peak wavelength of 315 nm at an irradiance of 0.3 W/m$^2$ for 6 hours in every daily photoperiod for 8 days. For 8 days of UV treatment, Treatment group 3 was irradiated with a total UV dose of about 51.84 kJ/m$^2$ for 8 days.

Treatment group 4 is a group of red leaf lettuce samples continuously irradiated with UV light having a peak wavelength of 315 nm at an irradiance of 0.6 W/m$^2$ for 6 hours in every daily photoperiod for 8 days. For 8 days of UV treatment, Treatment group 4 was irradiated with a total UV dose of about 103.68 kJ/m$^2$ for 8 days.

Treatment group 5 is a group of red leaf lettuce samples continuously irradiated with UV light having a peak wavelength of 385 nm at an irradiance of 30 W/m$^2$ for 8 days. For 8 days of UV treatment, Treatment group 5 was irradiated with a total UV dose of about 20,736 kJ/m$^2$ for 8 days.

Treatment group 6 is a group of red leaf lettuce samples irradiated with UV light having a peak wavelength of 295 nm at an irradiance of 0.1 W/m$^2$ by a pulse method in every photoperiod for 8 days. Here, the pulse method refers to a process of repeating UV treatment for 1.5 hours and UV treatment stop (UV treatment rest) for 1 hour. For 8 days of UV treatment, Treatment group 6 was irradiated with a total UV dose of about 17.28 kJ/m$^2$.

Experiment 1: Growth Variation Depending Upon UV Treatment Conditions

FIG. 1 is a graph depicting fresh weights of an aerial part of a plant according to UV treatment conditions.

The graph shows the fresh weights of an aerial part of red leaf lettuce for 8 days of UV treatment.

Referring to FIG. 1, there was no significant difference between all of Treatment groups 1 to 6 and a control group. That is, the UV treatment conditions of Treatment groups 1 to 6 were not detrimental conditions for growth of the red leaf lettuce.

Figure 2:
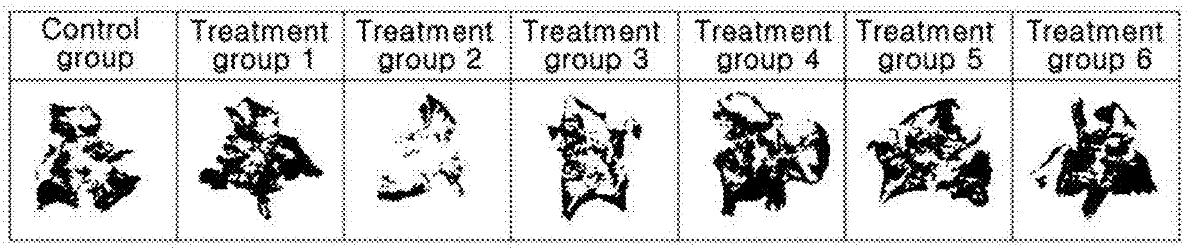
FIG. 2 is pictures of plants according to UV treatment conditions.

FIG. 2 is pictures of plants according to UV treatment conditions.

Referring to FIG. 2, it could be seen that Treatment group 1 and Treatment groups 3 to 6 exhibited a similar color to the control group. However, it could be seen that Treatment group 2 had a smaller red area and a larger green area than the control group.

Figure 3:
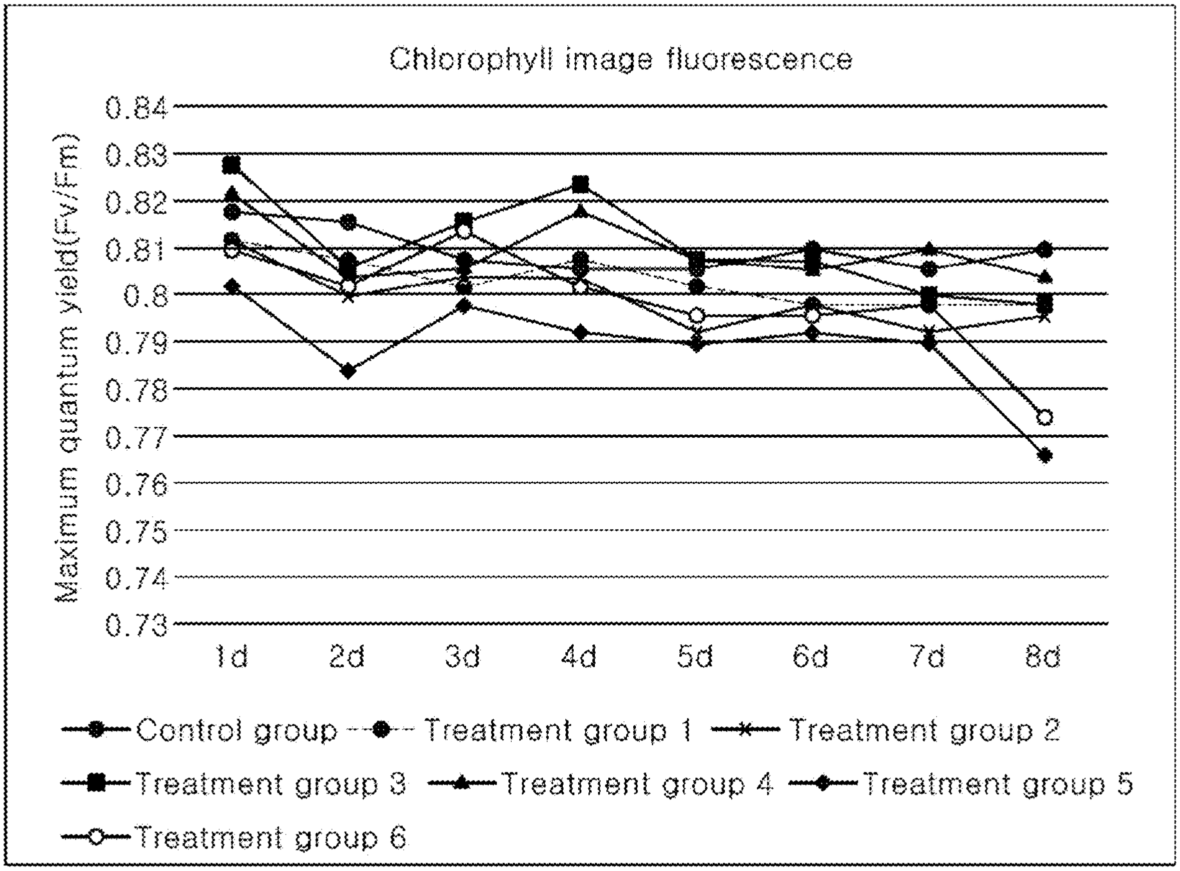
FIG. 3 is a graph depicting chlorophyll fluorescence of a plant according to UV treatment conditions.

FIG. 3 is a graph depicting chlorophyll fluorescence of a plant according to UV treatment conditions.

Referring to FIG. 3, Treatment group 1, Treatment group 3 and Treatment group 4 exhibited similar chlorophyll fluorescence (Fv/Fm) to the control group. In addition, the control group, Treatment group 1, Treatment group 3 and Treatment group 4 maintained a chlorophyll fluorescence of about 0.8.

Treatment group 2 maintained a chlorophyll fluorescence of less than 0.8 from day 5 under UV treatment. That is, referring to FIG. 2 and FIG. 3, it could be seen that Treatment group 2 suppressed exhibition of pigments and was subjected to excessive stress, as compared with the control group.

Treatment group 5 irradiated with UVA had a chlorophyll fluorescence of less than 0.8 on day 2 under UV treatment. As a result, it could be seen that UVA directly affected chlorophyll of plants. That is, it could be seen that the intensity of UVA used in Treatment group 5 had a negative influence upon the photosynthetic electron transport system of the plants.

Treatment group 6 maintained a chlorophyll fluorescence of about 0.8 from day 1 to day 7 and exhibited rapid decrease in chlorophyll fluorescence on day 8 under UV irradiation.

However, as shown in FIG. 2, since Treatment group 6 was grown to a similar level to the control group on day 8, it is believed that there was an error in measurement of the chlorophyll fluorescence of Treatment group 6 on day 8.

That is, it could be seen that Treatment group 6 was also grown to a similar level to the control group.

Based on experimental results of FIG. 1 to FIG. 3, it could be seen that Treatment group 1, Treatment group 3, Treatment group 4 and Treatment group 6 were grown to a similar level to the control group. As a result, it could be seen that the UV treatment conditions of Treatment group 1, Treatment group 3, Treatment group 4 and Treatment group 6 were not detrimental conditions for growth of plants.

Experiment 2: Change in Phytochemical Content Depending Upon UV Treatment Conditions FIG. 4 to FIG. 7 are graphs depicting change in phytochemical content of a plant according to UV treatment conditions.

Figure 4:
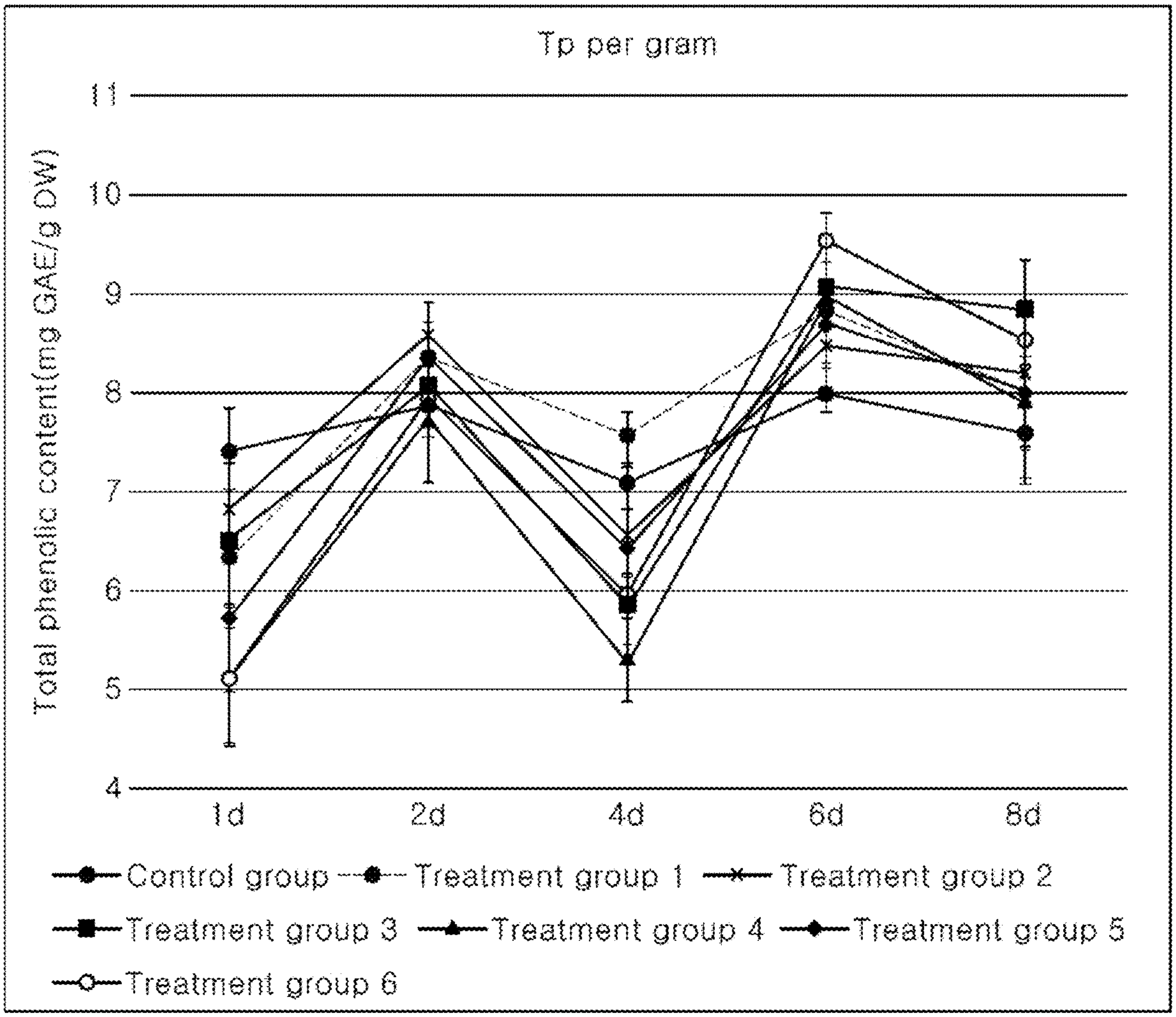
FIG. 4 is a graph depicting a total phenolic content per gram of plant according to UV treatment conditions.
Figure 5:
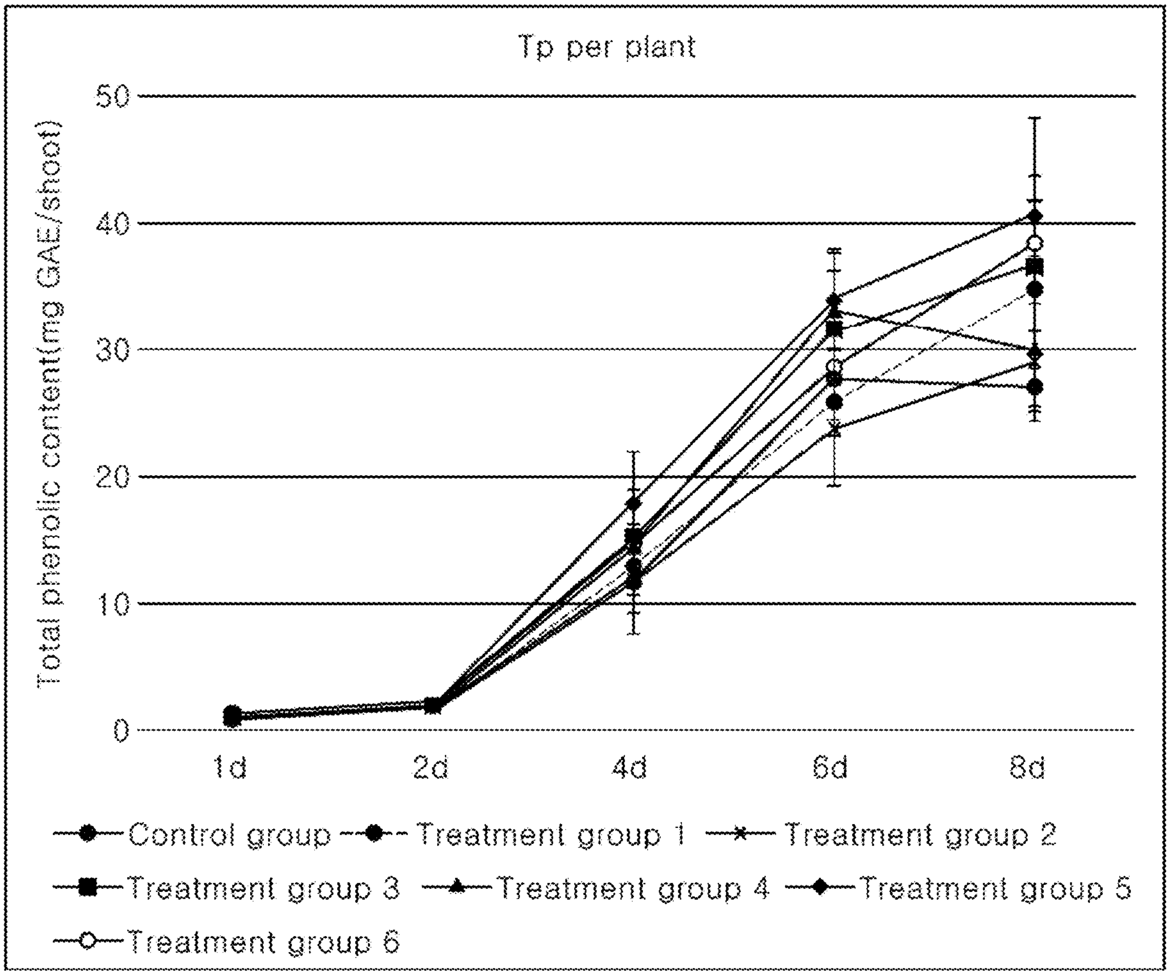
FIG. 5 is a graph depicting a total phenolic content per plant according to UV treatment conditions.

FIG. 4 is a graph depicting a total phenolic content (Tp) per gram of plant according to UV treatment conditions and FIG. 5 is a graph depicting a total phenolic content per plant according to UV treatment conditions.

Referring to FIG. 4, from day 2 under UV treatment, Treatment group 1 continued to have a greater total phenolic content per gram than the control group. In addition, from day 6 under UV treatment, all of Treatment groups 1 to 6 had greater total phenolic contents per gram than the control group. In particular, Treatment group 1 exhibited the highest total phenolic content on day 4 under UV treatment and Treatment group 6 exhibited the highest total phenolic content on day 6 under UV treatment.

Referring to FIG. 5, there was no significant difference in the total phenolic content per plant between each of Treatment groups 1 to 6 and the control group until day 6. However, on day 8, each of Treatment groups 1 to 6 exhibited a greater total phenolic content than the control group.

Figure 6:
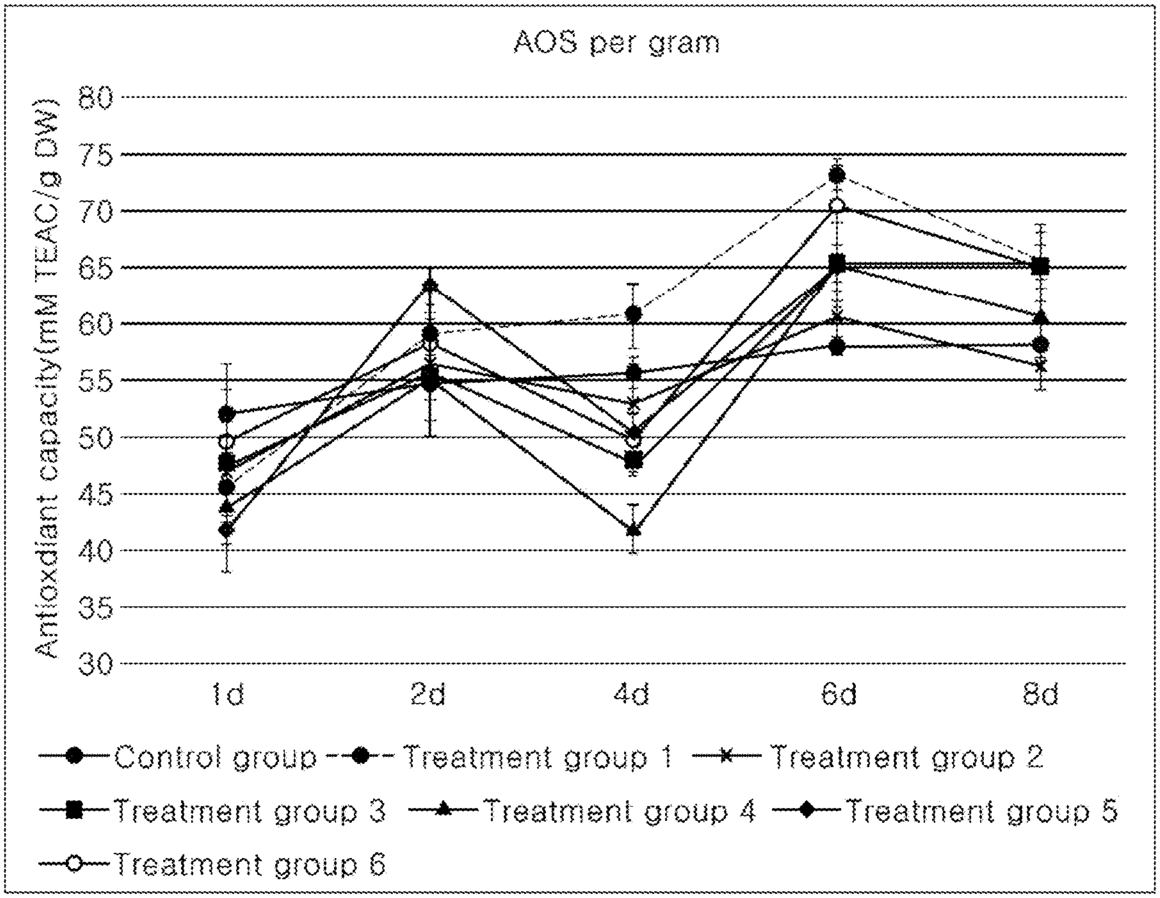
FIG. 6 is a graph depicting antioxidant capacity per gram of plant according to UV treatment conditions.
Figure 7:
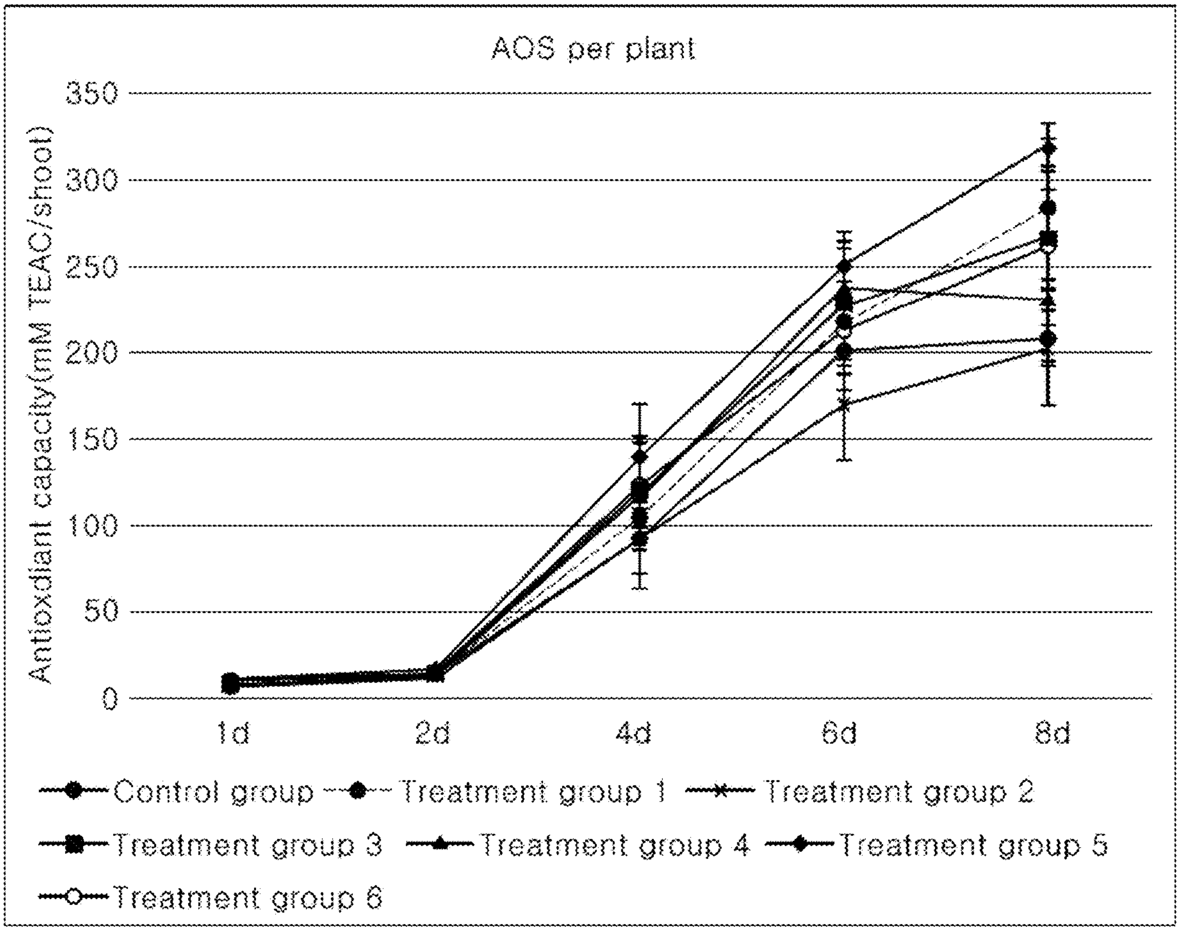
FIG. 7 is a graph depicting antioxidant capacity per plant according to UV treatment conditions.

FIG. 6 is a graph depicting antioxidant capacity (AOS) per gram of plant according to UV treatment conditions and FIG. 7 is a graph depicting antioxidant capacity per plant according to UV treatment conditions.

Referring to FIG. 6, Treatment groups 1 to 6 exhibited similar or greater antioxidant capacity per gram than the control group except for on day 1 and day 4 under UV treatment. In particular, Treatment group 1 exhibited the highest antioxidant capacity per gram on day 4 and day 6. In addition, Treatment group 2 exhibited the smallest antioxidant capacity per gram 4 days after UV treatment.

Referring to FIG. 7, there was no significant difference in antioxidant capacity per plant between each of Treatment groups 1 to 6 and the control group until day 4 under UV treatment. However, from day 6 under UV treatment, Treatment group 1 and Treatment groups 3 to 6 exhibited greater antioxidant capacity per plant than the control group. Here, Treatment group 2 had a smaller total phenolic content per plant than the control group from day 4 under UV treatment.

From the experimental results of FIG. 4 to FIG. 7, it could be seen that each of Treatment group 1 and Treatment group 3 to Treatment group 6 had a similar or greater phytochemical content than the control group. In particular, both Treatment group 1 and Treatment group 6 had greater total phenolic contents and greater antioxidant capacity than the control group.

Experiment 3: Analysis of Second Metabolite According to UV Treatment Conditions FIG. 8 and FIG. 9 show graphs depicting analysis result of second metabolites depending upon UV treatment conditions.

To this end, different metabolites between the control group and each of the treatment groups were monitored through partial least squares discriminant analysis (PLS-DA). (VIP>0.7, p-value<0.05)

Figure 8:
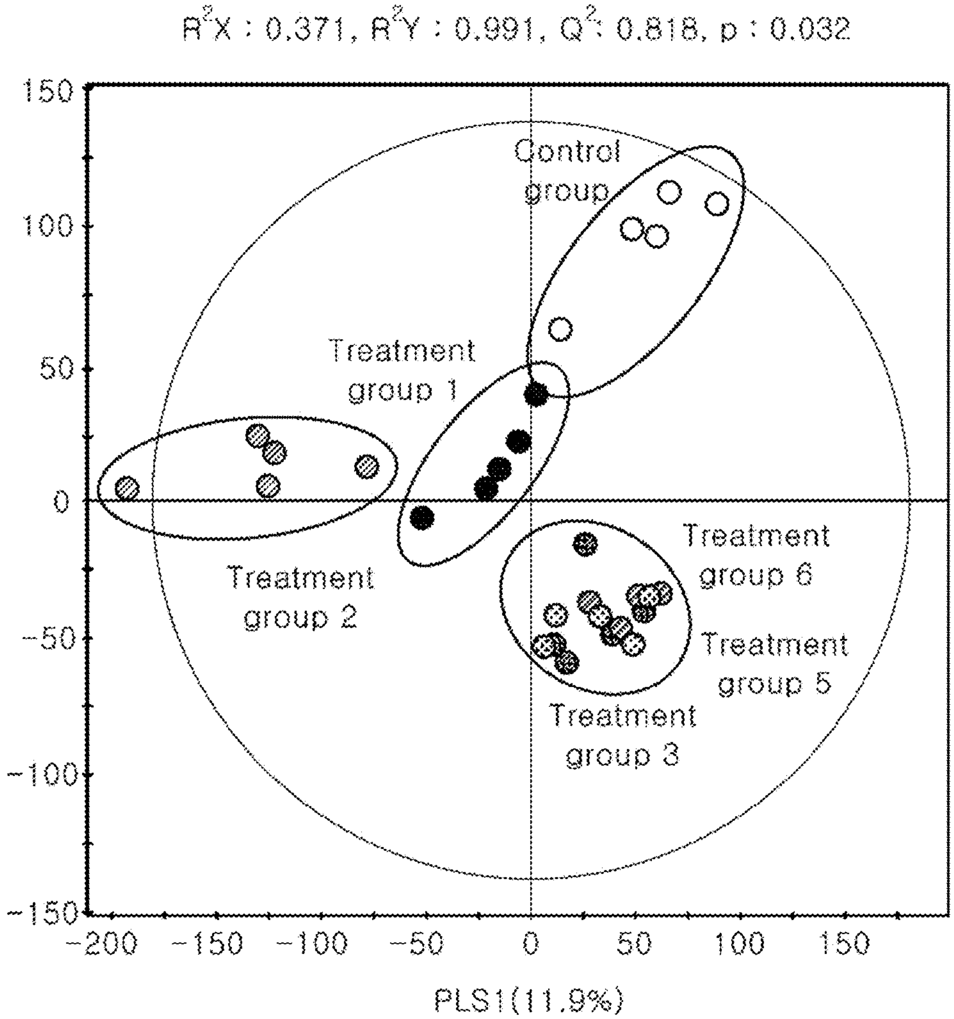
FIG. 8 is a graph depicting an analysis result of differences in second metabolites in a plant on day 4 under UV treatment.
Figure 9:
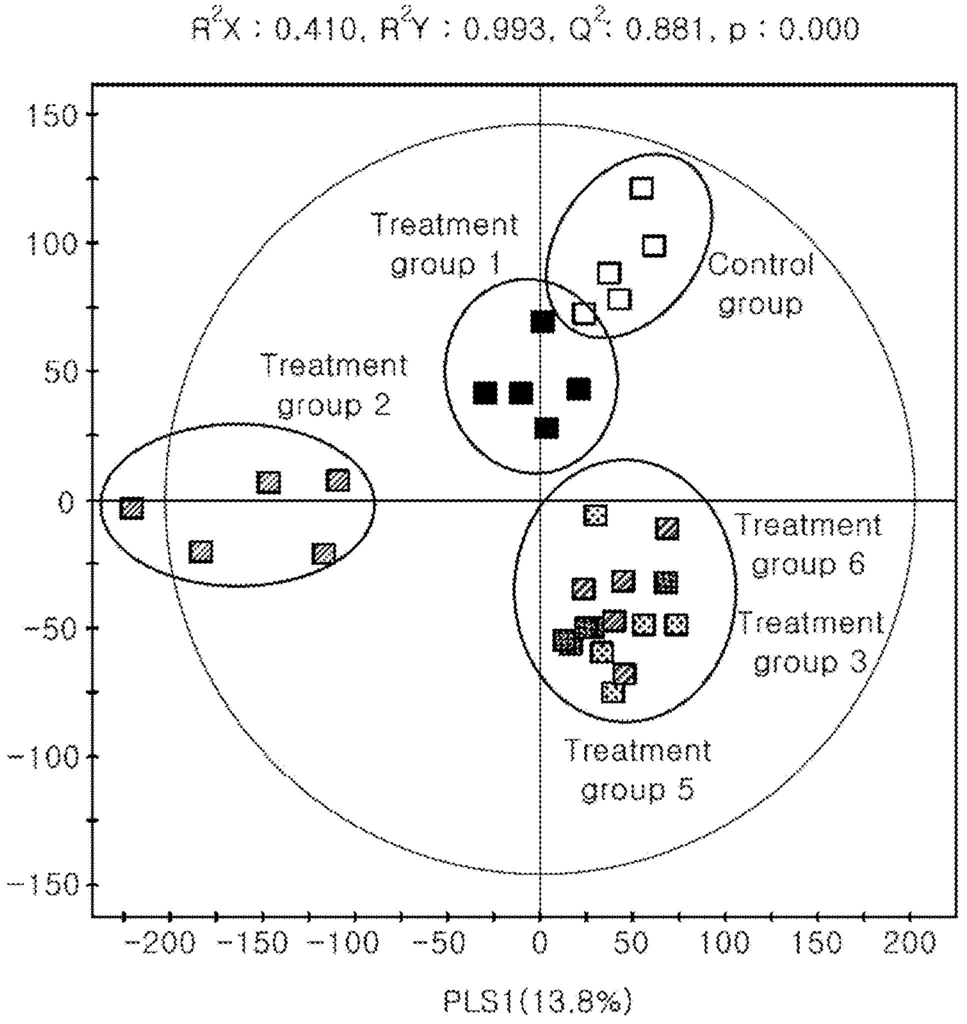
FIG. 9 is a graph depicting an analysis result of differences in second metabolites in a plant on day 8 under UV treatment.
Figure 10:
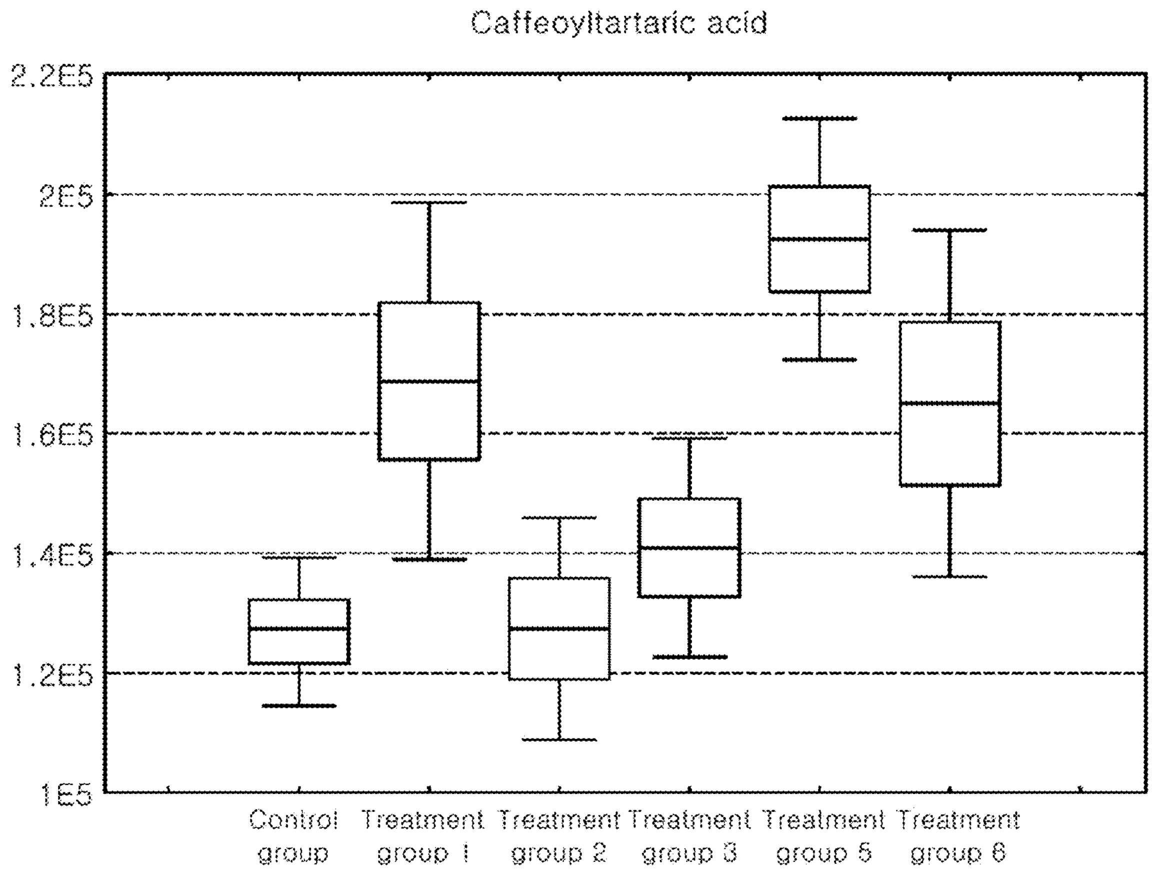
FIG. 10 to FIG. 13 are graphs depicting analysis results of hydroxycinnamic acid-based metabolites according to conditions on day 4 under UV treatment.
Figure 11:
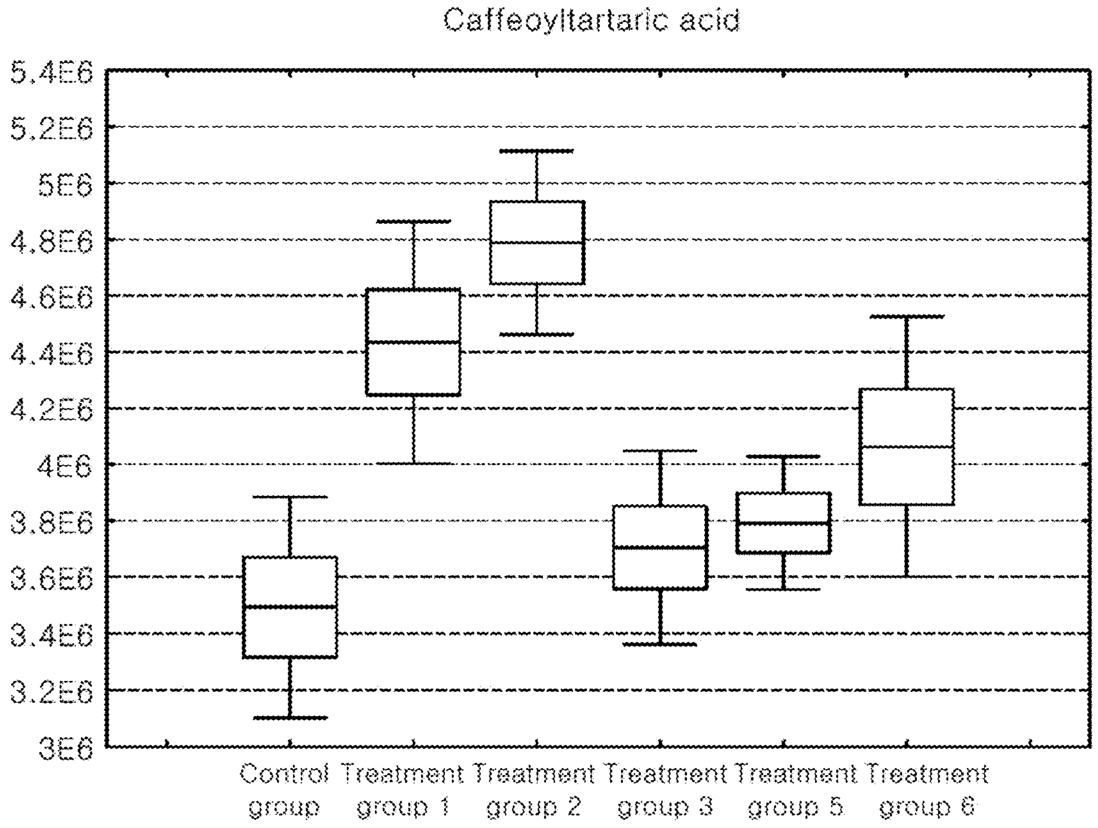
Figure 12:
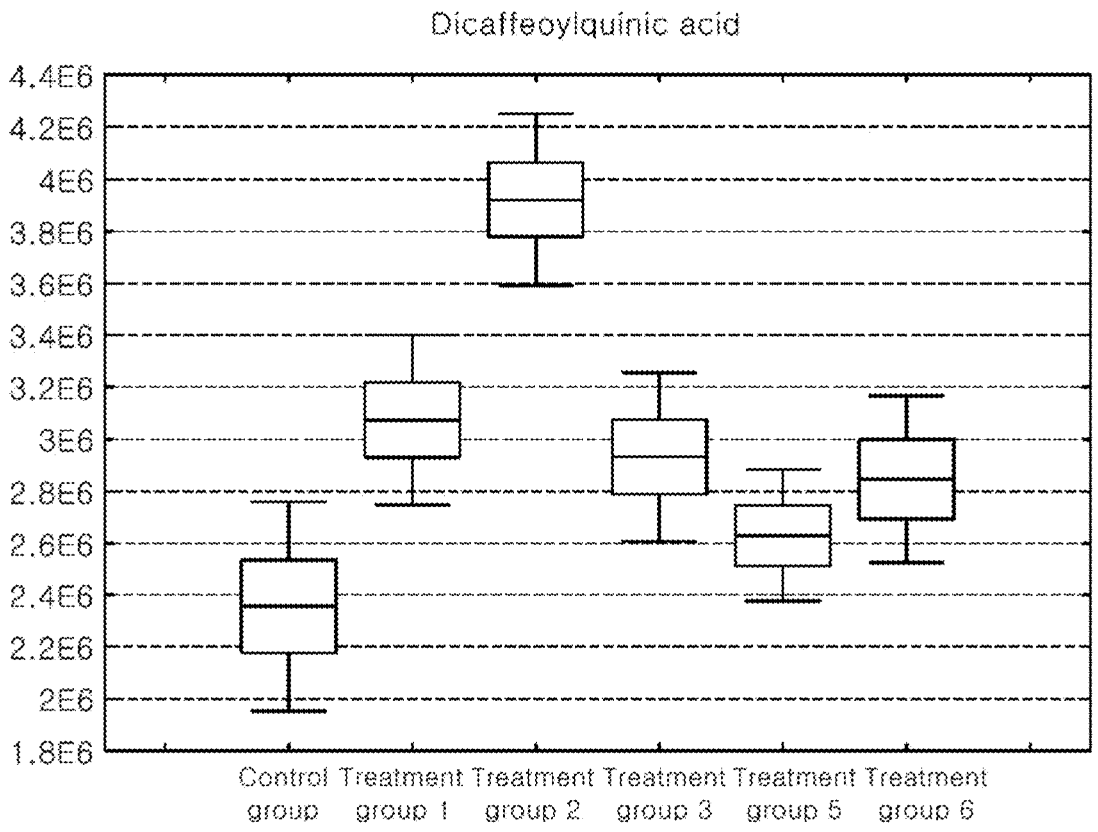
Figure 13:
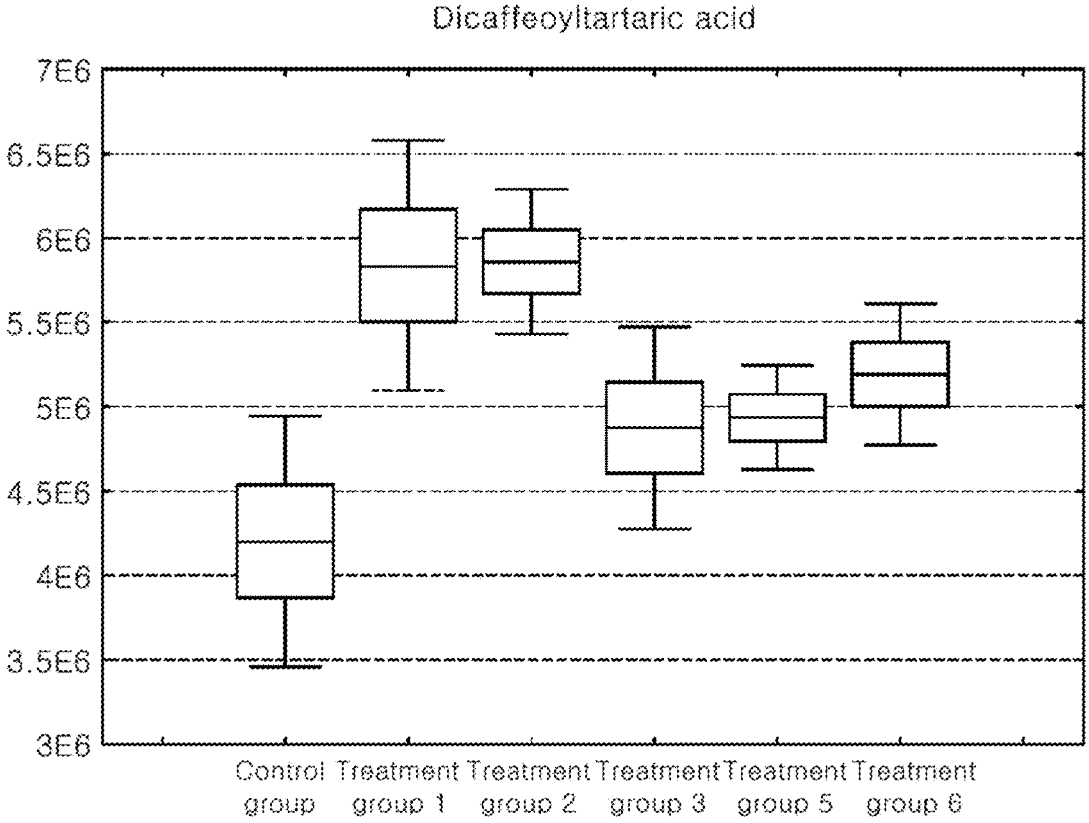

FIG. 8 is a graph depicting an analysis result of differences in second metabolites in a plant on day 4 under UV treatment and FIG. 9 is a graph depicting an analysis result of differences in second metabolites in a plant on day 8 under UV treatment.

Referring to FIG. 8 and FIG. 9, PCA results on day 4 and day 8 under UV treatment are classified into 4 groups.

The four groups include a group consisting of the control group, a group consisting of Treatment group 1, a group consisting of Treatment group 2, and a group consisting of Treatment group 3, Treatment group 5 and Treatment group 6. That is, as a result of metabolite analysis, Treatment group 3 and Treatment group 6 irradiated with UVB become the same group as Treatment group 5 irradiated with UVA.

In addition, variation of the second metabolite according to the UV treatment conditions was analyzed through LC-MS analysis.

FIG. 10 to FIG. 23 show analysis results of second metabolites of a plant on day 4 under UV treatment.

FIG. 10 to FIG. 13 are graphs depicting analysis results of hydroxycinnamic acid-based metabolites according to conditions on day 4 under UV treatment.

Referring to FIG. 10 to FIG. 13, it could be seen that the contents of caffeoyltartaric acid, caffeoylquinic acid and dicaffeoyltartaric acid were much greater in Treatment group 1 than in the control group. In addition, the contents of caffeoylquinic acid, dicaffeoylquinic acid and dicaffeoyltartaric acid were very much greater in Treatment group 2 than in the control group.

That is, the contents of caffeoylquinic acid and dicaffeoyltartaric acid were significantly increased in Treatment group 1 and Treatment group 2.

In addition, the content of caffeoyltartaric acid was also greater in Treatment group 5 than in the control group.

However, although the content of caffeoyltartaric acid was greater in Treatment group 3, Treatment group 5 and Treatment group 6 than in the control group, the contents of other metabolites in these treatment groups were similar to the contents thereof in the control group.

Figure 14:
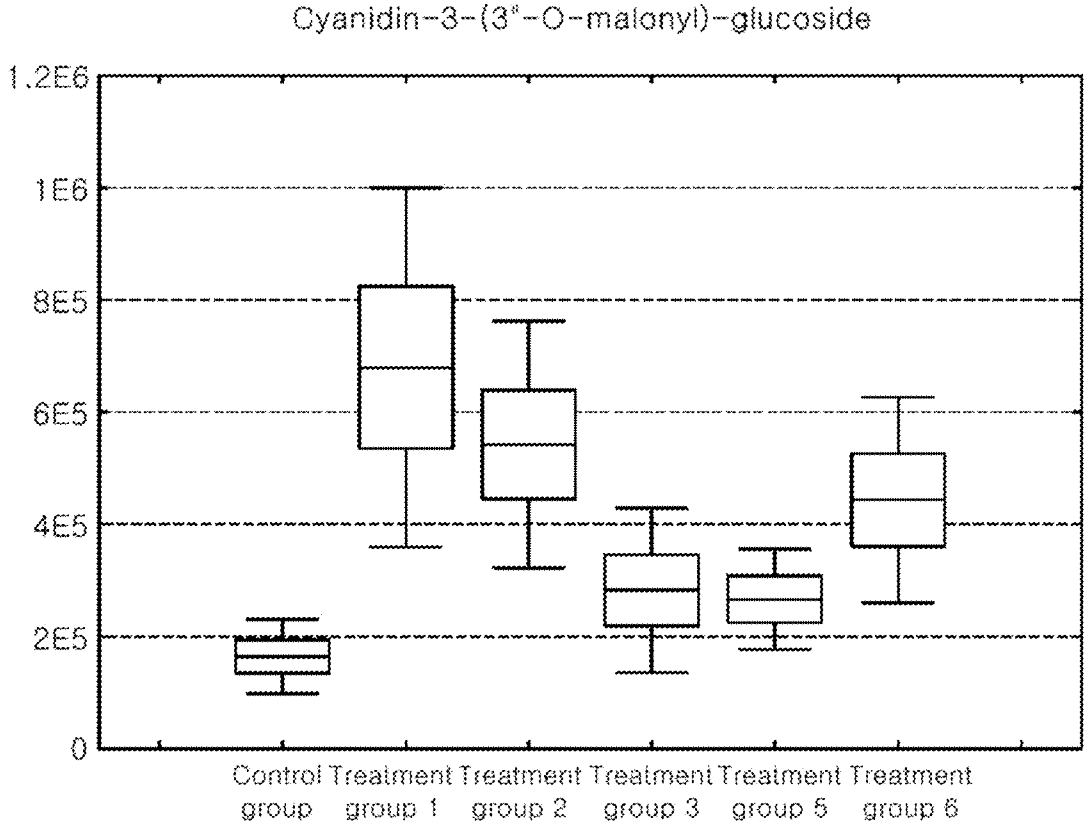
FIG. 14 is a graph depicting analysis results of anthocyanin-based metabolites according to conditions on day 4 under UV treatment.

FIG. 14 is a graph depicting analysis results of anthocyanin-based metabolites according to conditions on day 4 under UV treatment.

Referring to FIG. 14, it could be seen that the content of cyanidin-3(3"-O-malonyl)-glucoside was greater in Treatment group 1, Treatment group 2 and Treatment group 6 than in the control group and was slightly greater or similar in the other treatment groups to the content thereof in the control group.

FIG. 15 to FIG. 20 are graphs depicting analysis results of flavonoid-based metabolites according to conditions on day 4 under UV treatment.

Figure 20:
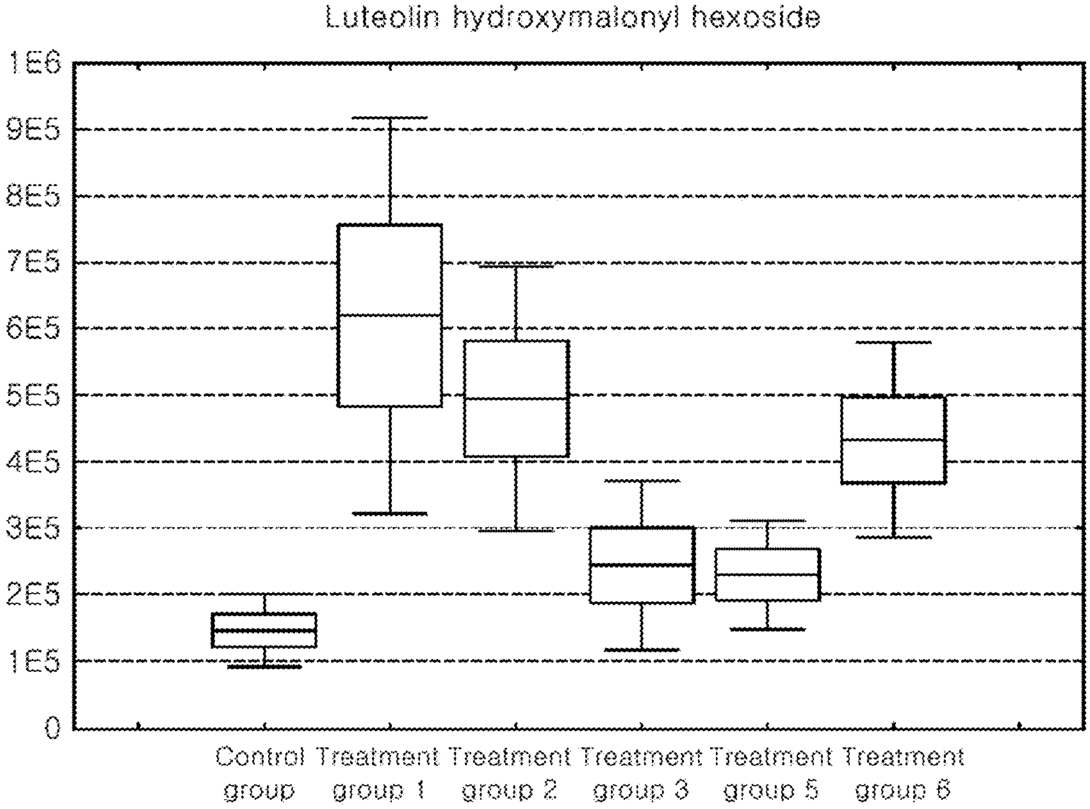

First, referring to FIG. 20, the content of luteolin hydroxy malonyl hexoside was greater in all of the treatment groups than in the control group.

Figure 16:
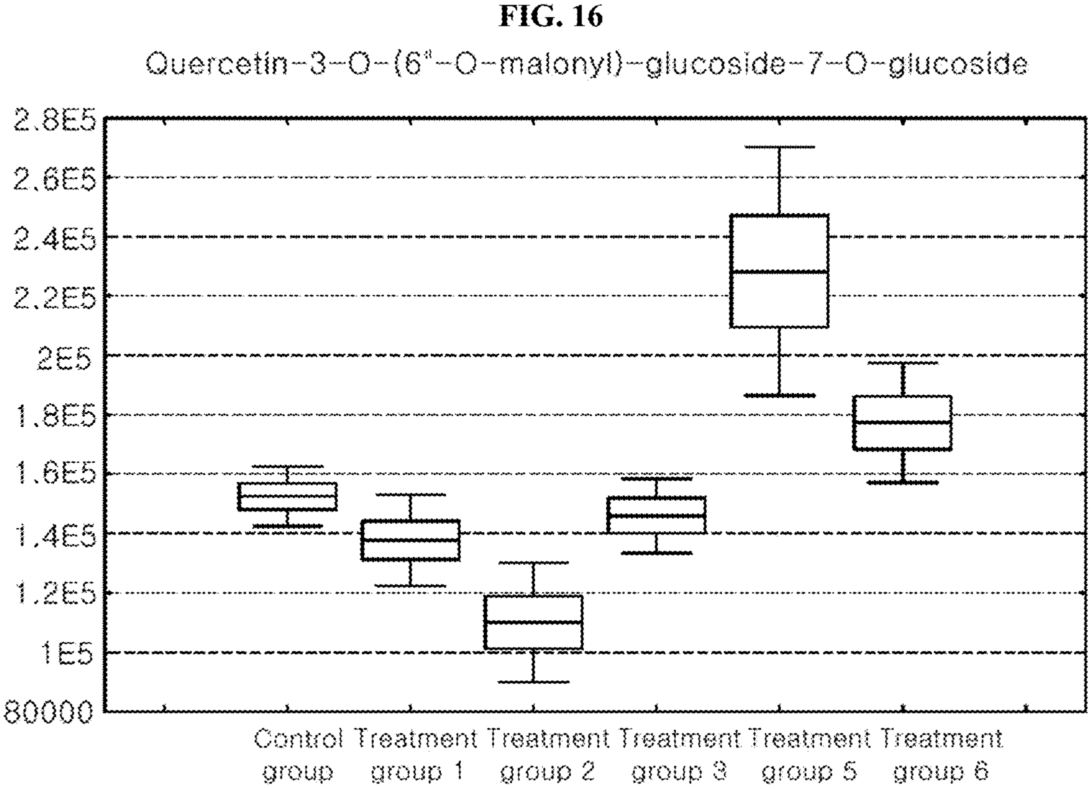

Referring to FIG. 16, the content of quercetin-3-O-(6"-O-malonyl)-glucoside-7-O-glucoside was greater in Treatment group 5 than in the control group and was smaller or similar in the other treatment groups to the content thereof in the control group.

Figure 19:
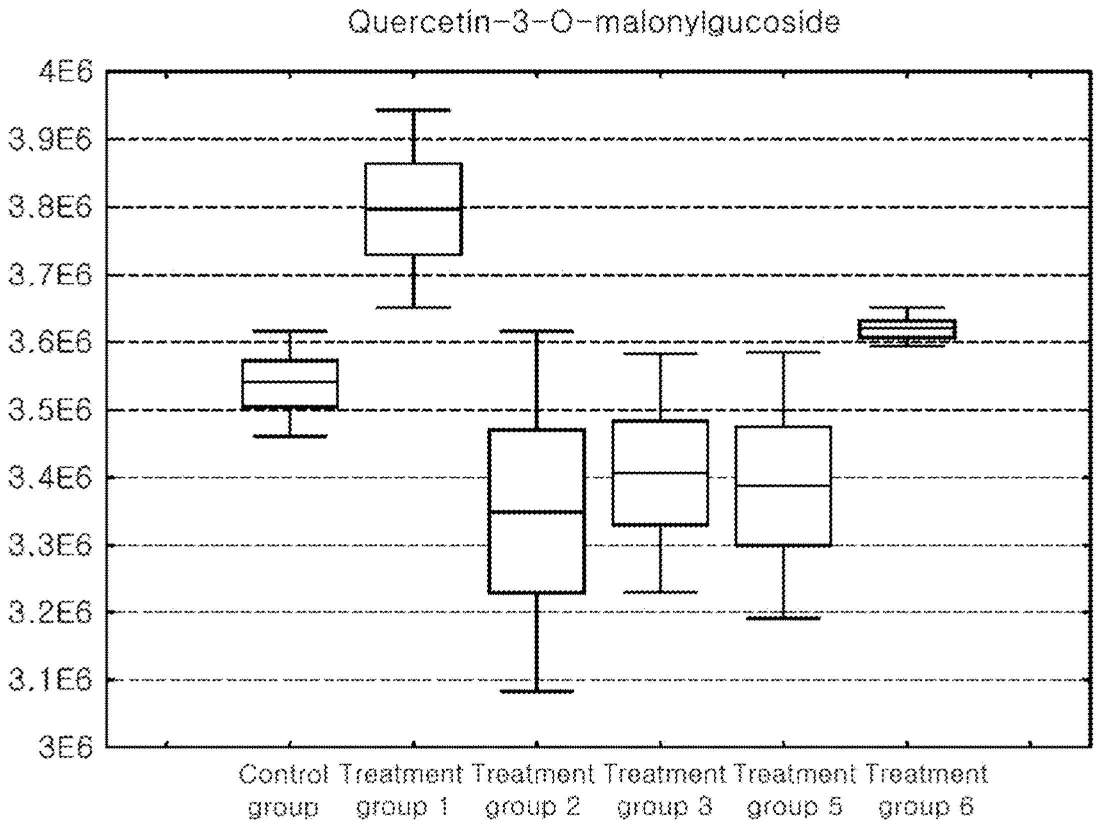

Further, referring to FIG. 19, the content of quercetin-3-O-malonylglucoside was greater in Treatment group 1 than in the control group and was smaller or similar in the other treatment groups to the content thereof in the control group.

Figure 15:
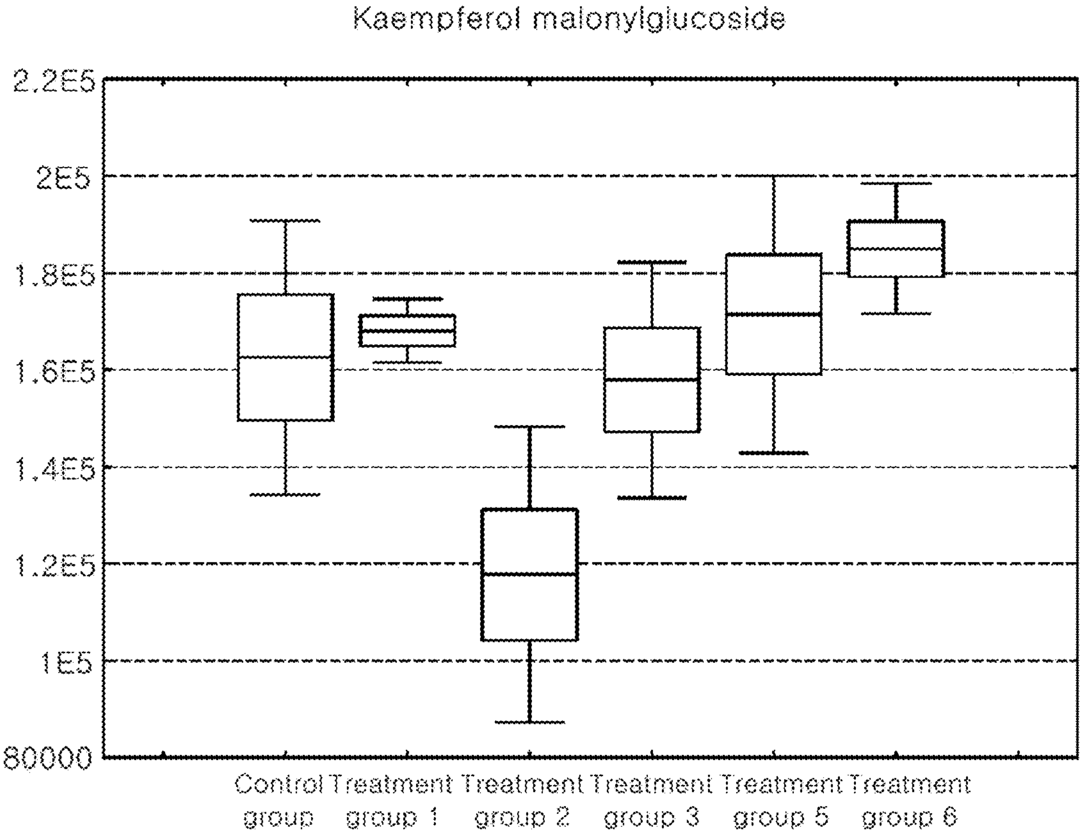
FIG. 15 to FIG. 20 are graphs depicting analysis results of flavonoid-based metabolites according to conditions on day 4 under UV treatment.
Figure 17:
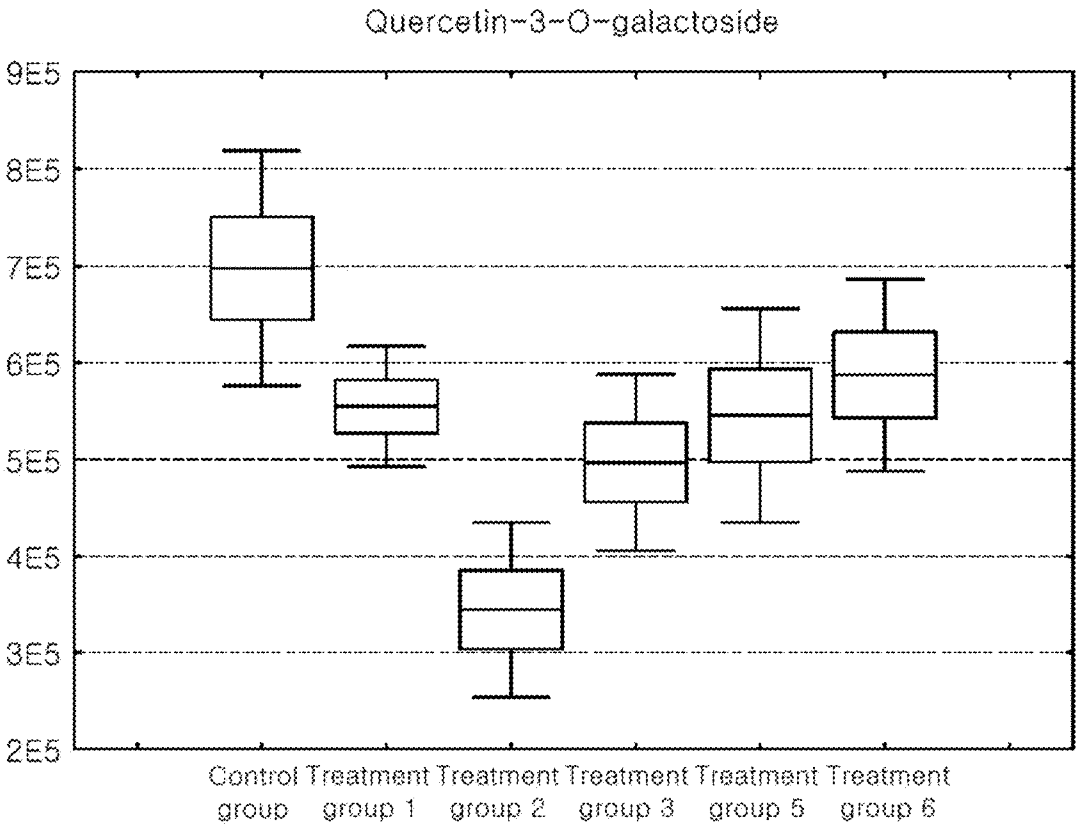
Figure 18:
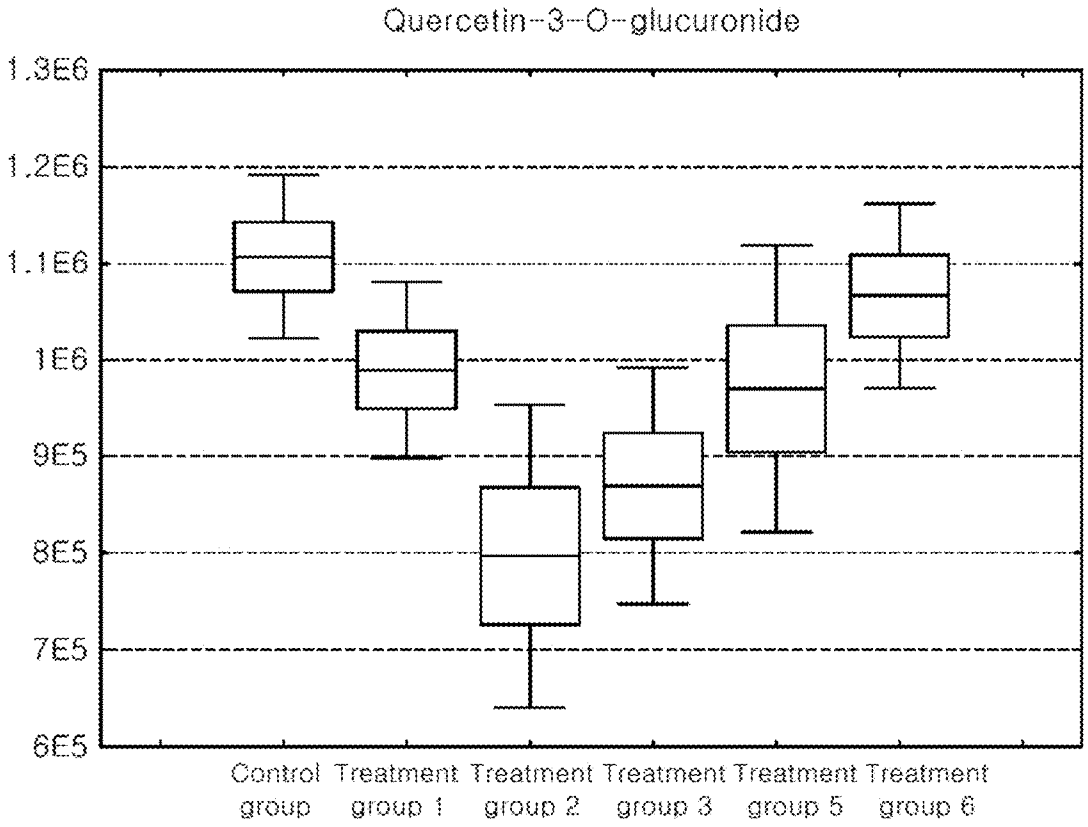

Referring to FIG. 15, FIG. 17 and FIG. 18, the contents of kaempferol malonyl glucoside, quercetin-3-O-galactoside and quercetin-3-O-galactoside in all of the treatment groups were greater or similar to the contents thereof in the control group.

Figure 21:
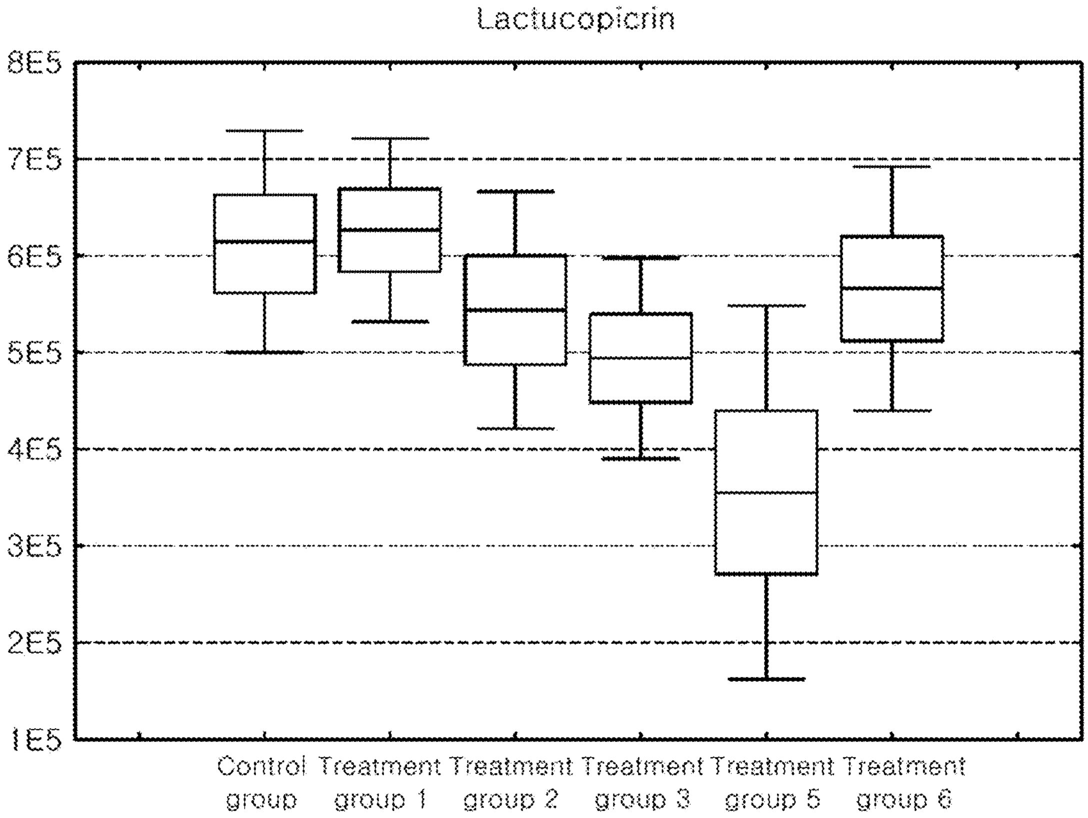
FIG. 21 to FIG. 23 are graphs depicting analysis results of sesquiterpene lactone-based metabolites and other metabolites according to conditions on day 4 under UV treatment.
Figure 22:
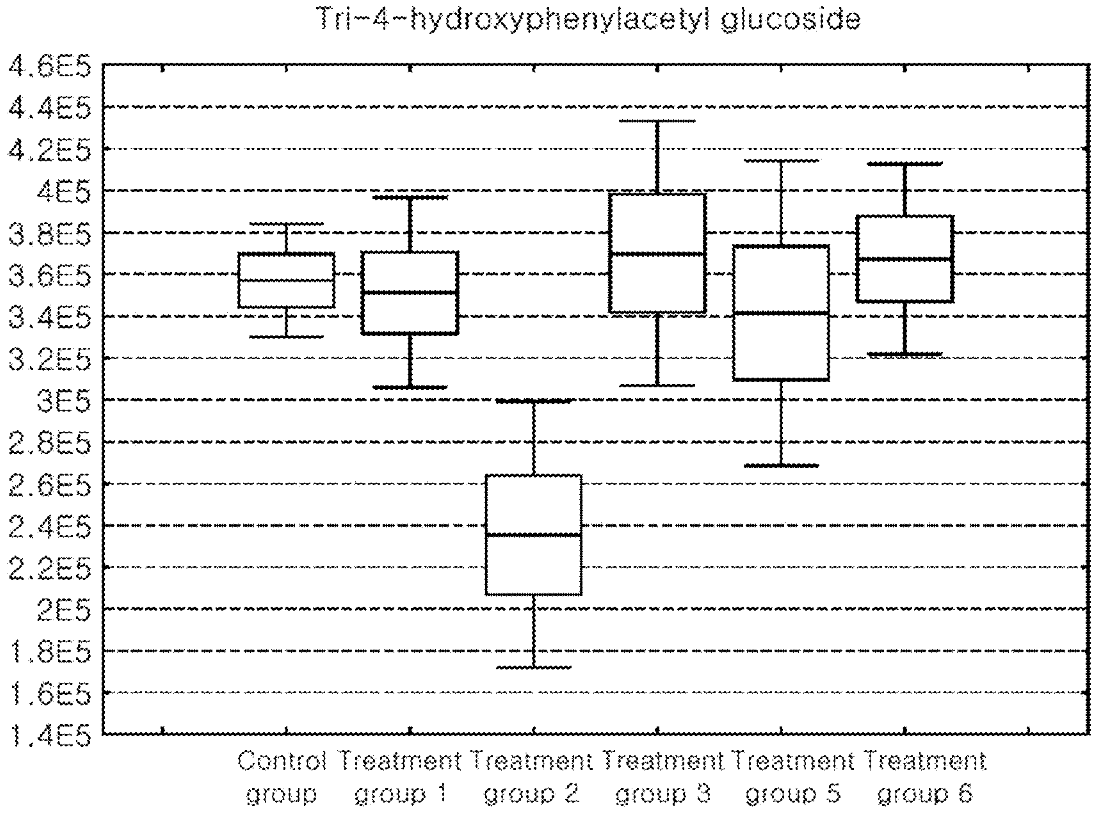
Figure 23:
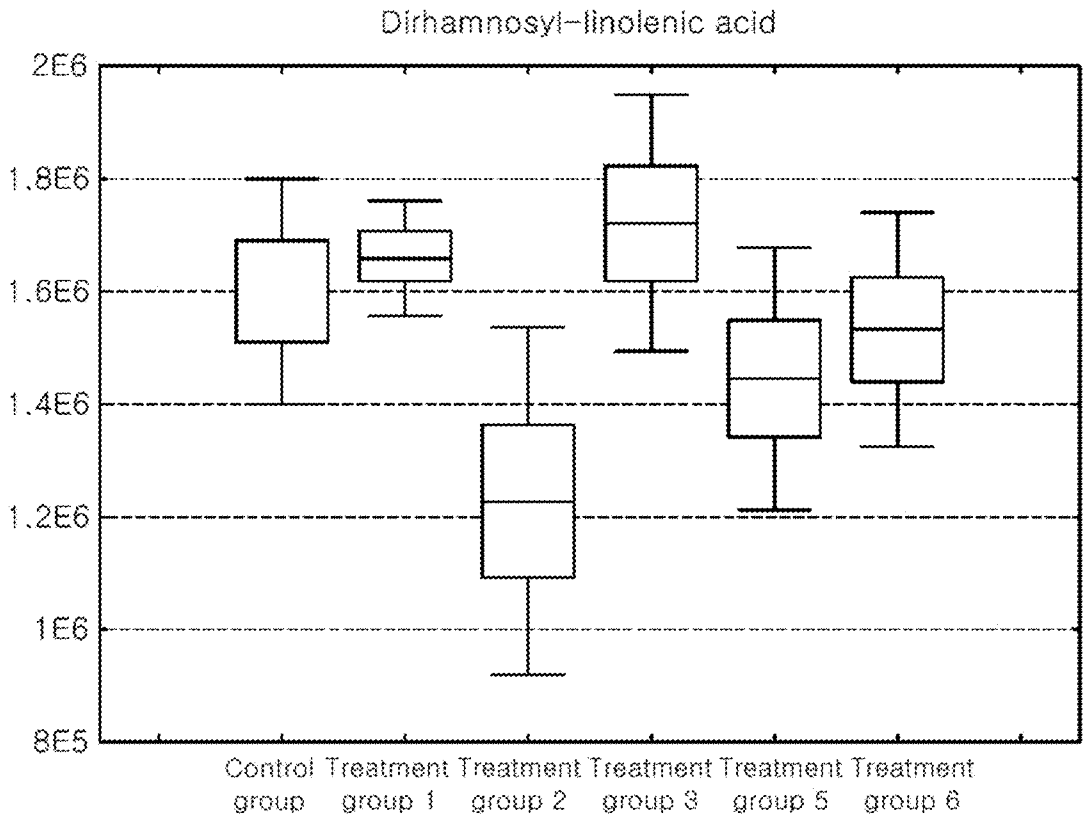

FIG. 21 to FIG. 23 are graphs depicting analysis results of sesquiterpene lactone-based metabolites and other metabolites according to conditions on day 4 under UV treatment.

Referring to FIG. 21, the content of lactucopicrin was slightly smaller in Treatment group 2, Treatment group 3 and Treatment group 6 irradiated with light in the UVB wavelength band than in the control group, and was much smaller in Treatment group 5 irradiated with light in the UVA wavelength band than in the control group.

The content of lactucopicrin in Treatment group 1 was similar to the content thereof in the control group.

Referring to FIG. 22 and FIG. 23, it could be seen that, although the contents of tri-4-hydroxyphenylacetyl glucoside and dirhamnosyl-linolenic acid in Treatment group 1, Treatment group 3, Treatment group 5 and Treatment group 6 were similar to the contents thereof in the control group, Treatment group 2 exhibited significant reduction in the contents thereof.

It could be seen that both UVA and UVB increased the contents of hydroxycinnamic acid-based metabolites and anthocyanin-based metabolites through change of the second metabolites on day 4 under UV treatment. In particular, light having a peak wavelength of 295 nm significantly increased the contents of hydroxycinnamic acid-based metabolites.

In addition, light having a peak wavelength of 295 nm and an intensity of 0.1 W increased the contents of quercetin-3-O-malonylglucoside and luteolin hydroxymalonyl hexoside, which are flavonoid-based metabolites.

UVA increased the contents of hydroxycinnamic acid-based caffeoyltartaric acid and flavonoid-based quercetin-3-O-(6"-O-malonyl)-glucoside-7-O-glucoside more than UVB.

In addition, light having a peak wavelength of 295 nm and an intensity of 0.3 W significantly decreased the contents of flavonoid-based quercetin-3-O-malonylglucoside and luteolin hydroxymalonyl hexoside.

Further, UVA significantly decreased the content of sesquiterpene lactone-based lactucopicrin.

FIG. 24 to FIG. 37 are graphs depicting analysis results of second metabolites according to conditions on day 8 under UV treatment.

FIG. 24 to FIG. 27 are graphs depicting analysis results of flavonoid-based metabolites according to conditions on day 8 under UV treatment.

Referring to FIG. 24 to FIG. 27, all of the treatment groups had similar or greater contents of hydroxycinnamic acid-based metabolites than the control group.

Figure 24:
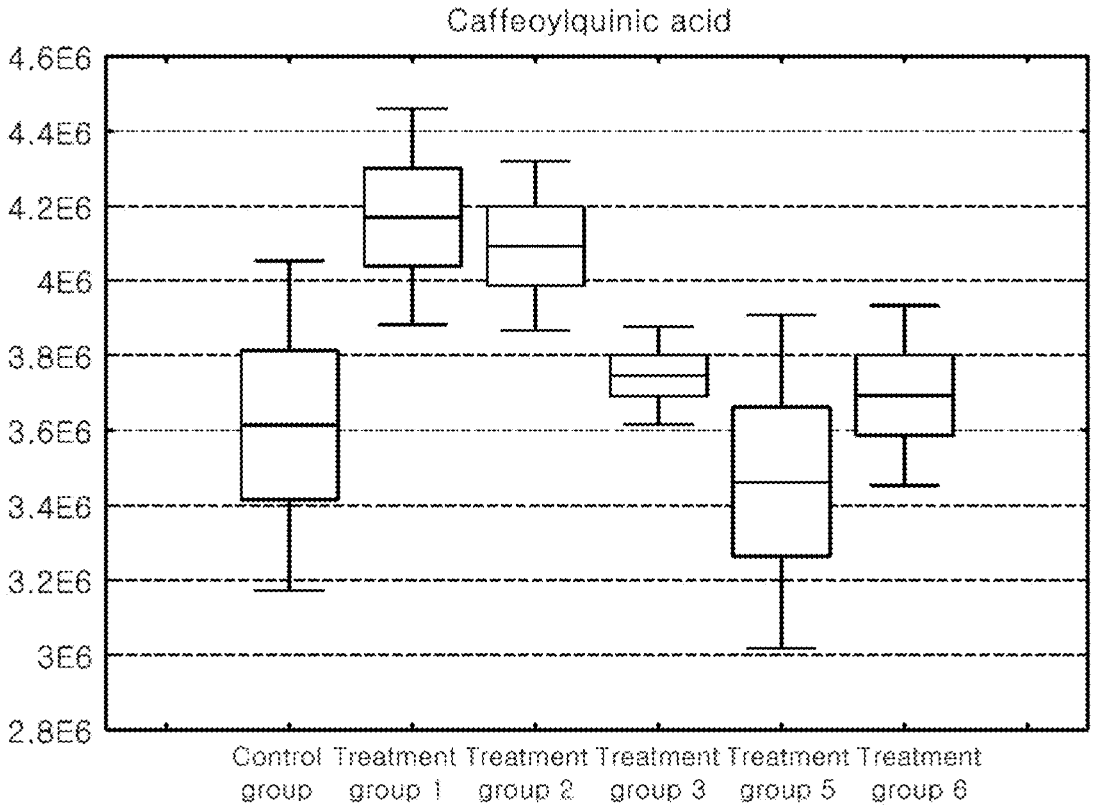
FIG. 24 to FIG. 27 are graphs depicting analysis results of hydroxycinnamic acid-based metabolites according to conditions on day 8 under UV treatment.
Figure 25:
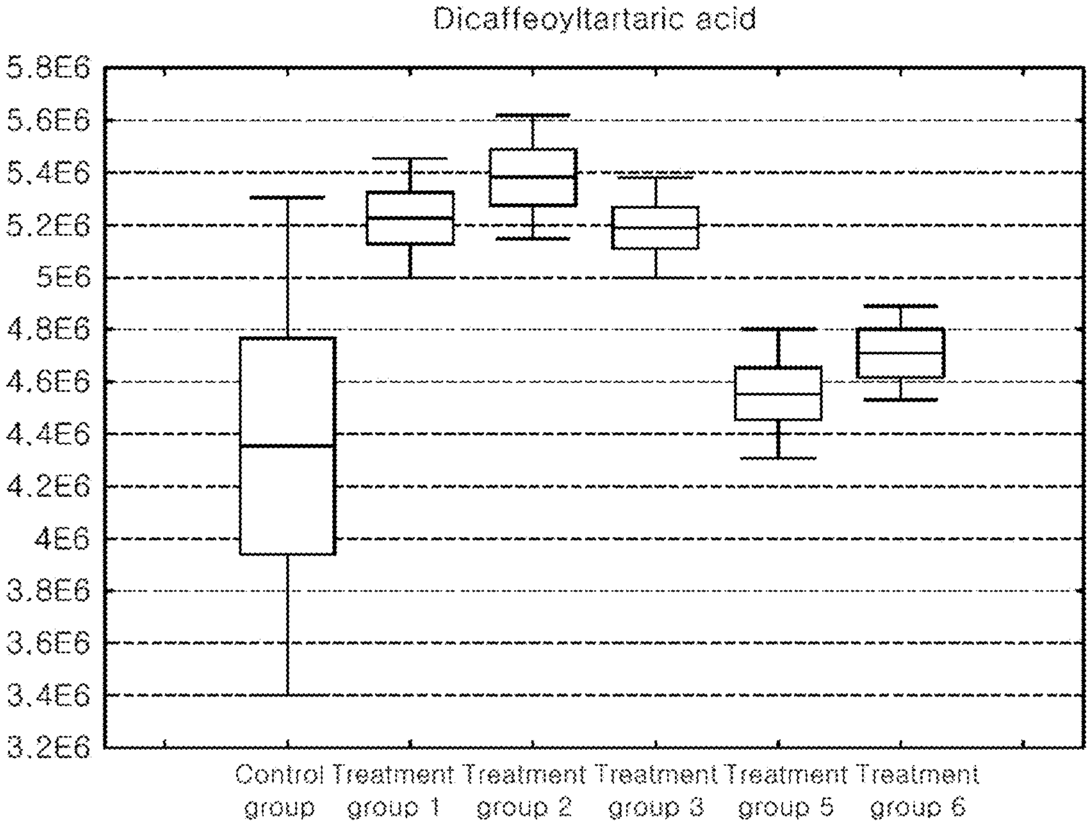

In particular, referring to FIG. 24, the content of caffeoylquinic acid in Treatment group 3, Treatment group 5 and Treatment group 6 was similar to the content thereof in the control group, and was greater in Treatment group 1 and Treatment group 2 than in the control group.

Figure 26:
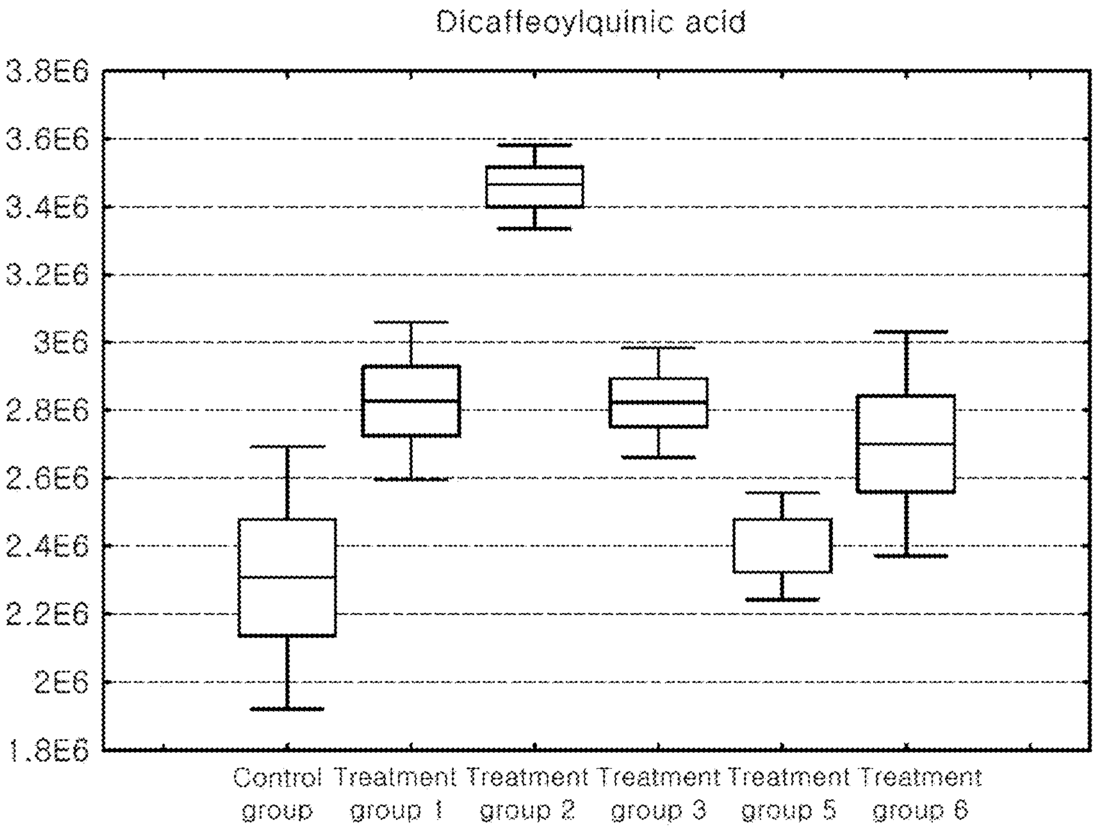

Referring to FIG. 26, Treatment group 2 had a greater content of dicaffeoylquinic acid than the control group.

Figure 27:
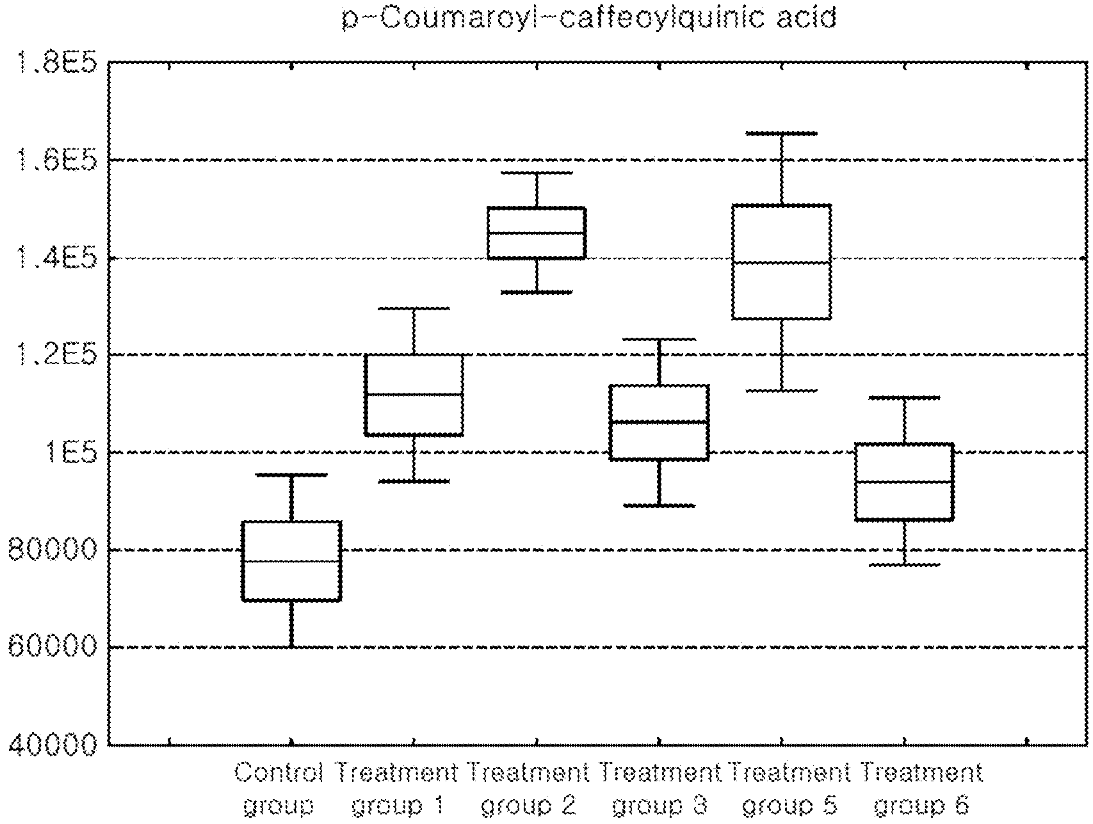

Referring to FIG. 27, Treatment group 2 and Treatment group 5 had a particularly high content of p-coumaroyl-caffeoylquinic acid.

Figure 28:
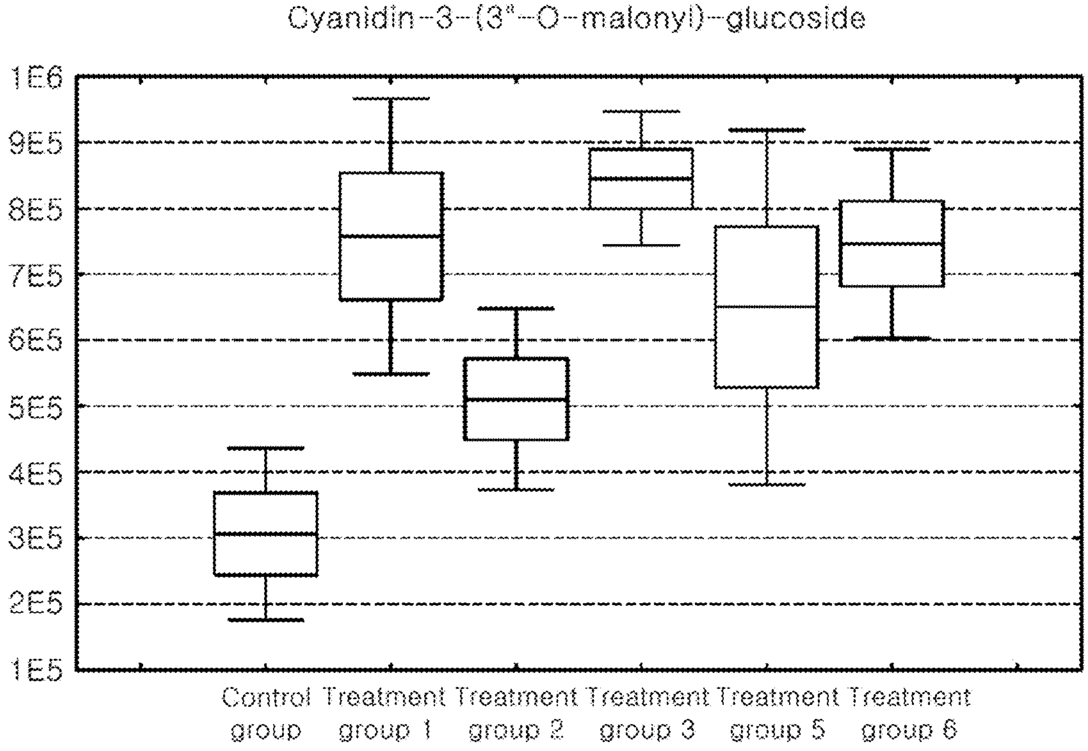
FIG. 28 is a graph depicting analysis results of anthocyanin-based metabolites according to conditions on day 8 under UV treatment.

FIG. 28 is a graph depicting analysis results of anthocyanin-based metabolites according to conditions on day 8 under UV treatment.

Referring to FIG. 28, all of the treatment groups had a greater content of cyanidin-3-(3"-O-malonyl)-glucoside than the control group.

FIG. 29 to FIG. 34 are graphs depicting analysis results of flavonoid-based metabolites according to conditions on day 8 under UV treatment.

Figure 31:
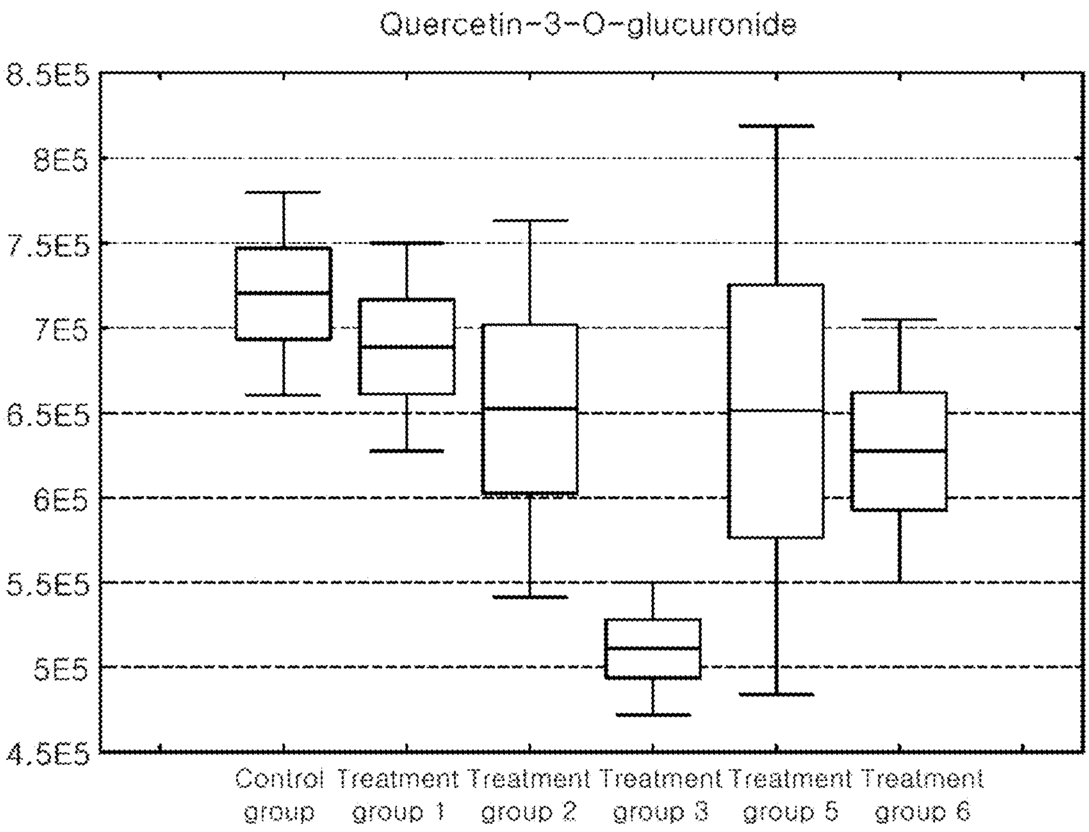
Figure 32:
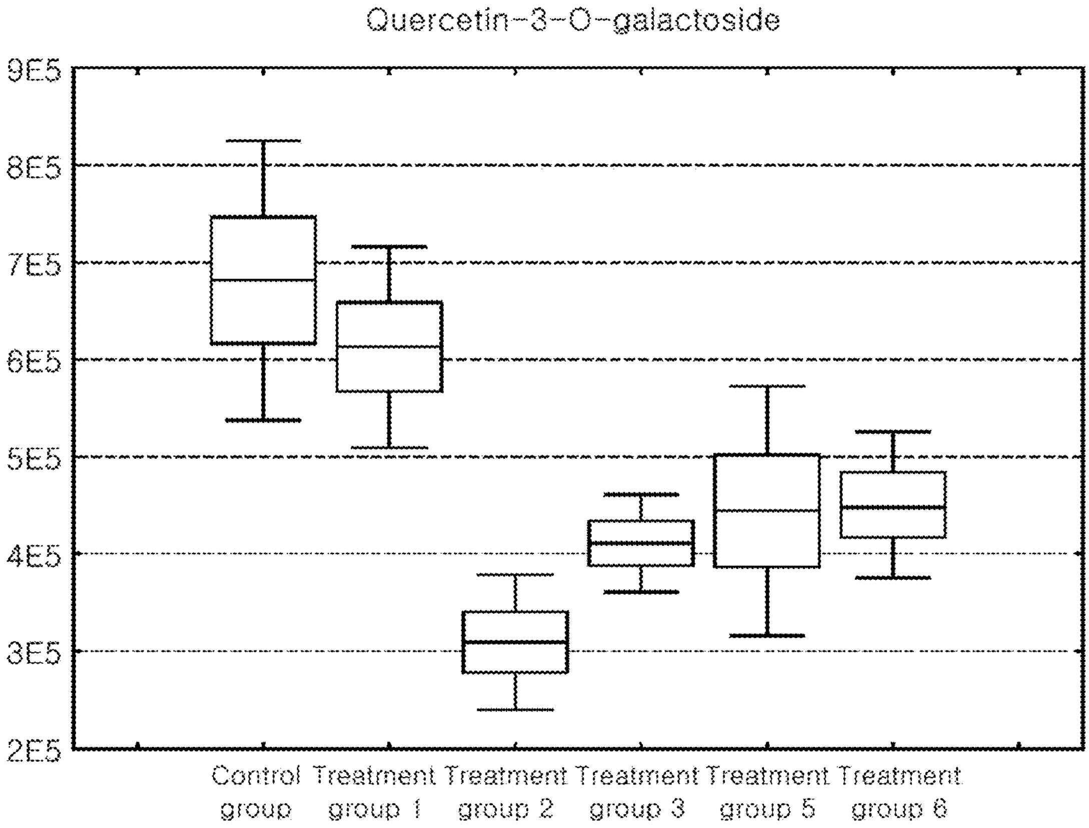
Figure 34:
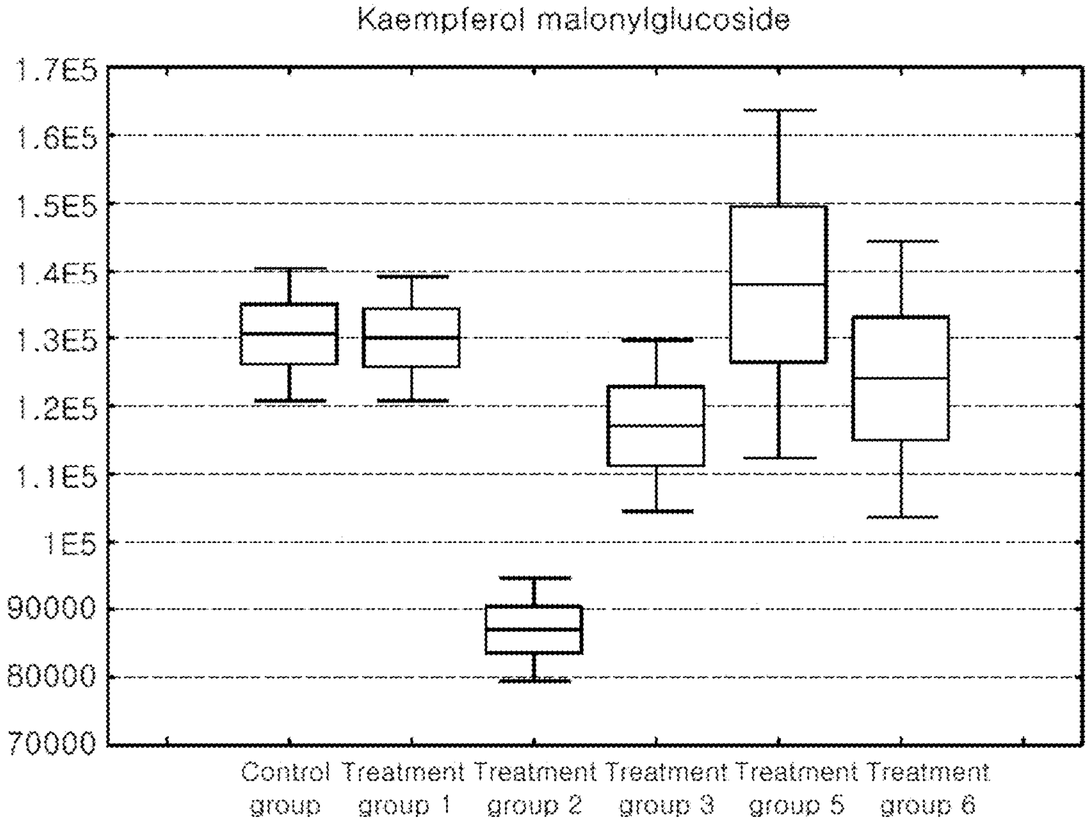

FIG. 31, FIG. 32 and FIG. 34 show that the contents of querecetin-3-O-glucuronide, quercetin-3-O-galactoside and kaempferol malonylglucoside in all of the treatment groups were similar to or smaller than the contents thereof in the control group.

Figure 29:
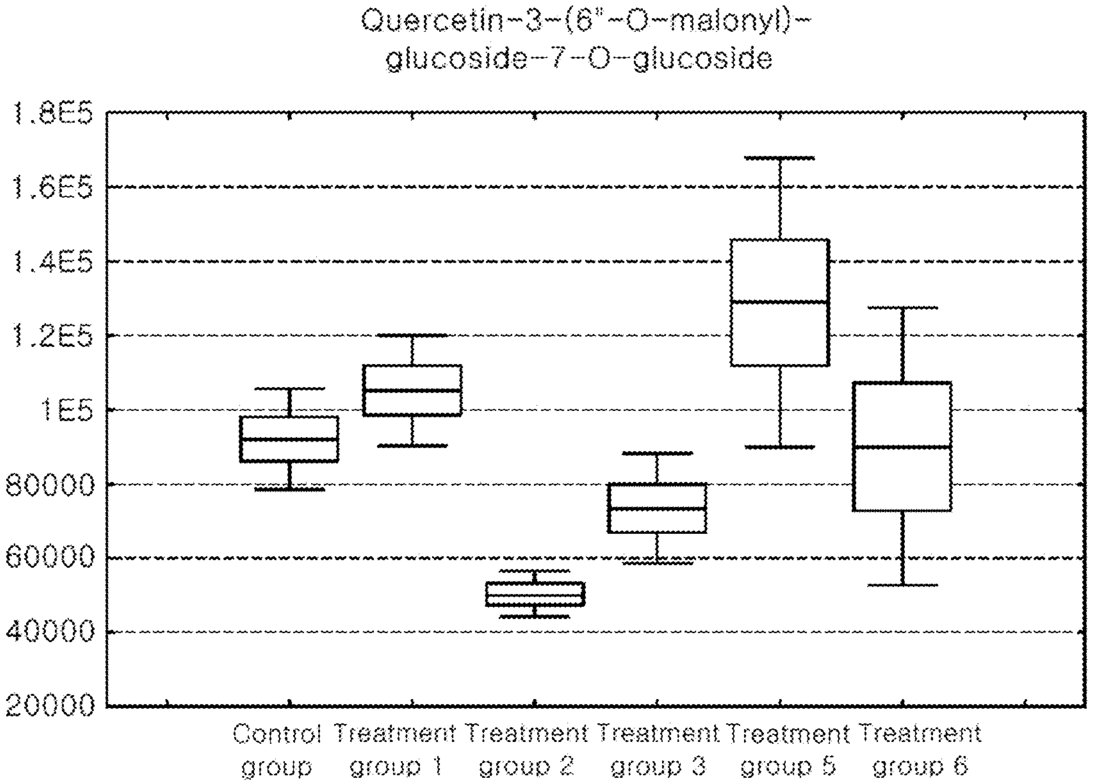
FIG. 29 to FIG. 34 are graphs depicting analysis results of flavonoid-based metabolites according to conditions on day 8 under UV treatment.

Referring to FIG. 29, the content of quercetin-3-O-(6"-O-malonyl)-glucoside-7-O-glucoside was similar in Treatment group 1, Treatment group 5 and Treatment group 6 to the content thereof in the control group and was smaller in Treatment group 2 and Treatment group 3 than in the control group.

Figure 30:
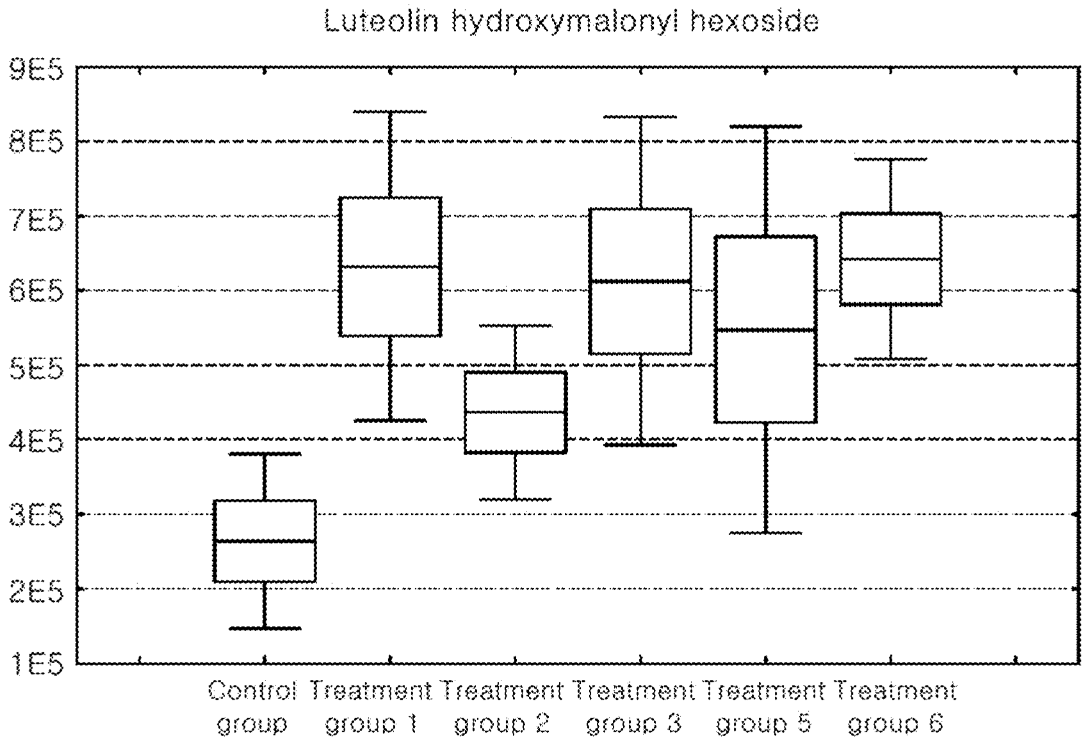

Referring to FIG. 30, the content of luteolin hydroxymalonyl hexoside was greater in all of the treatment groups than in the control group.

Figure 33:
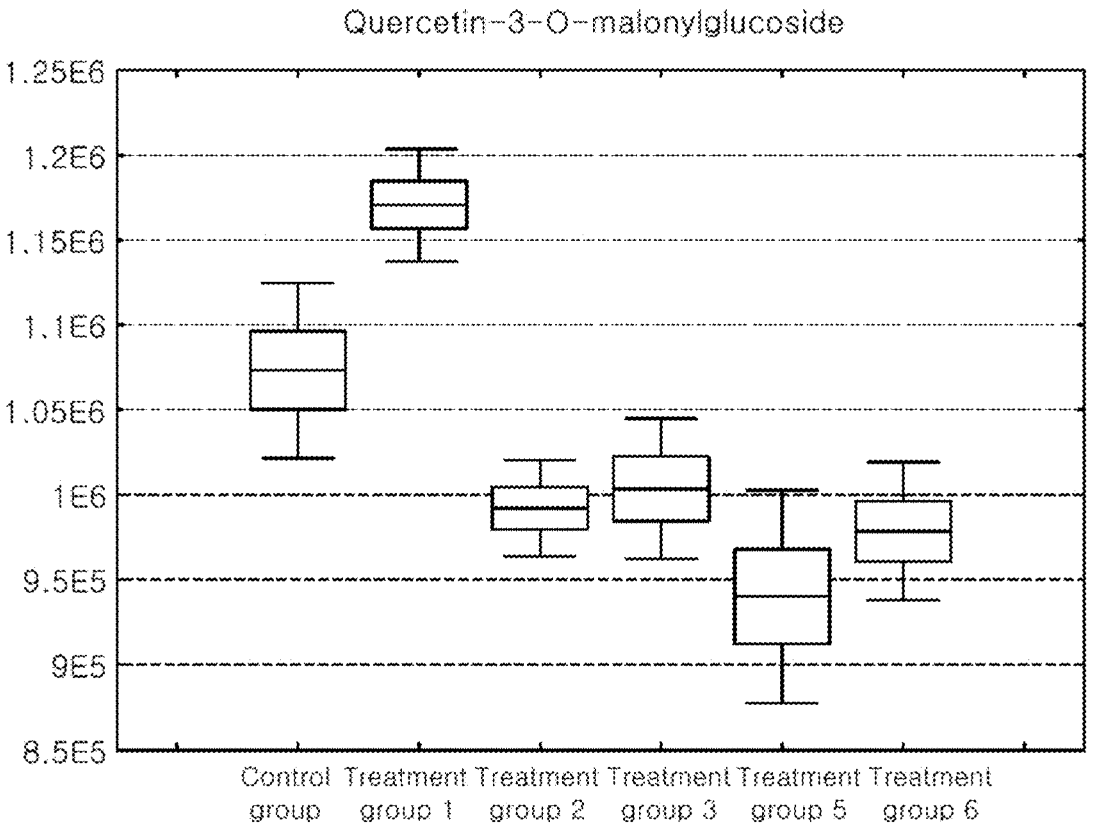

Referring to FIG. 33, the content of quercetin-3-O-malonylglucoside was greater in Treatment group 1 than in the control group and was smaller in the other treatment groups than in the control group.

Figure 35:
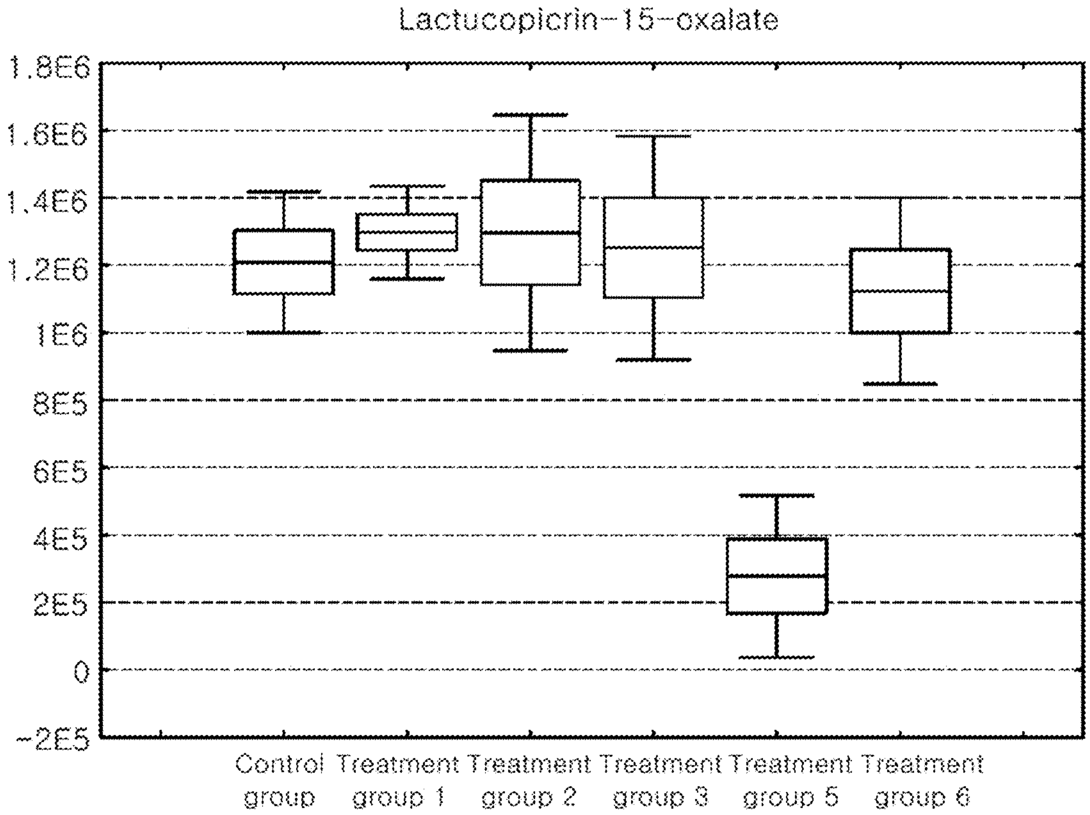
FIG. 35 to FIG. 37 are graphs depicting analysis results of sesquiterpene lactone-based metabolites and other metabolites according to conditions on day 8 under UV treatment.
Figure 36:
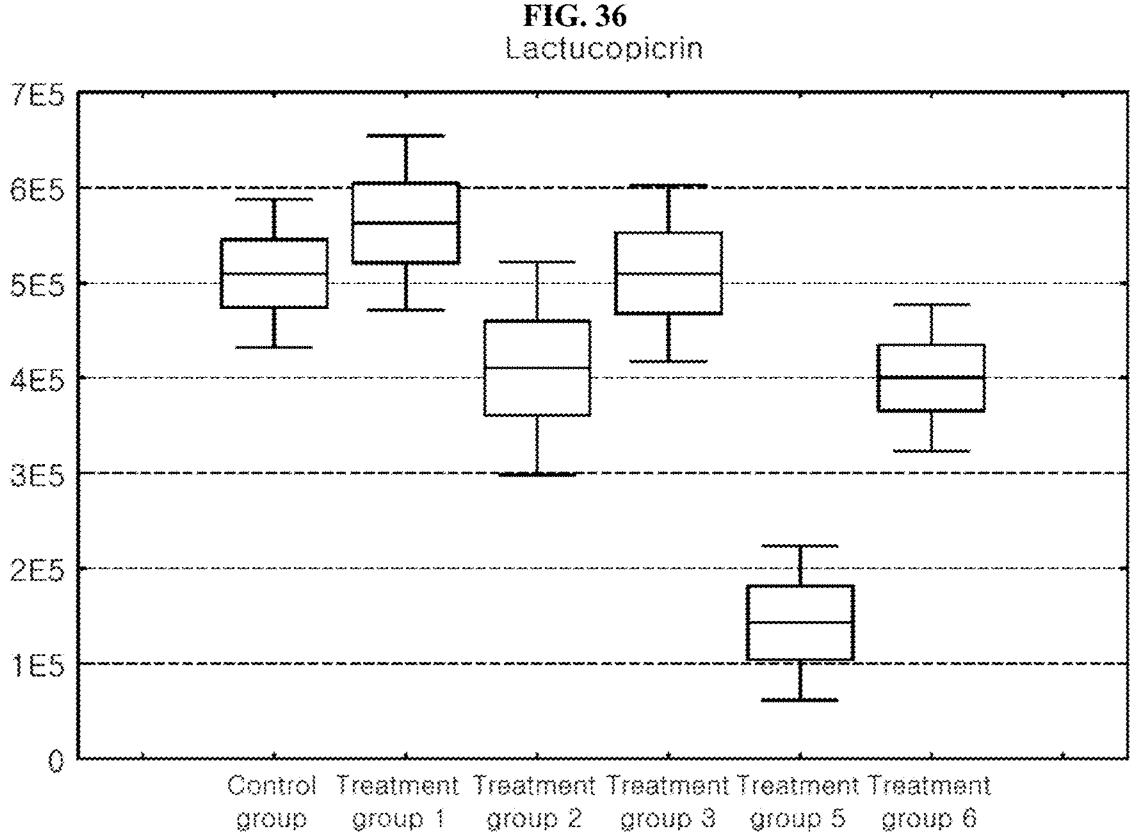
Figure 37:
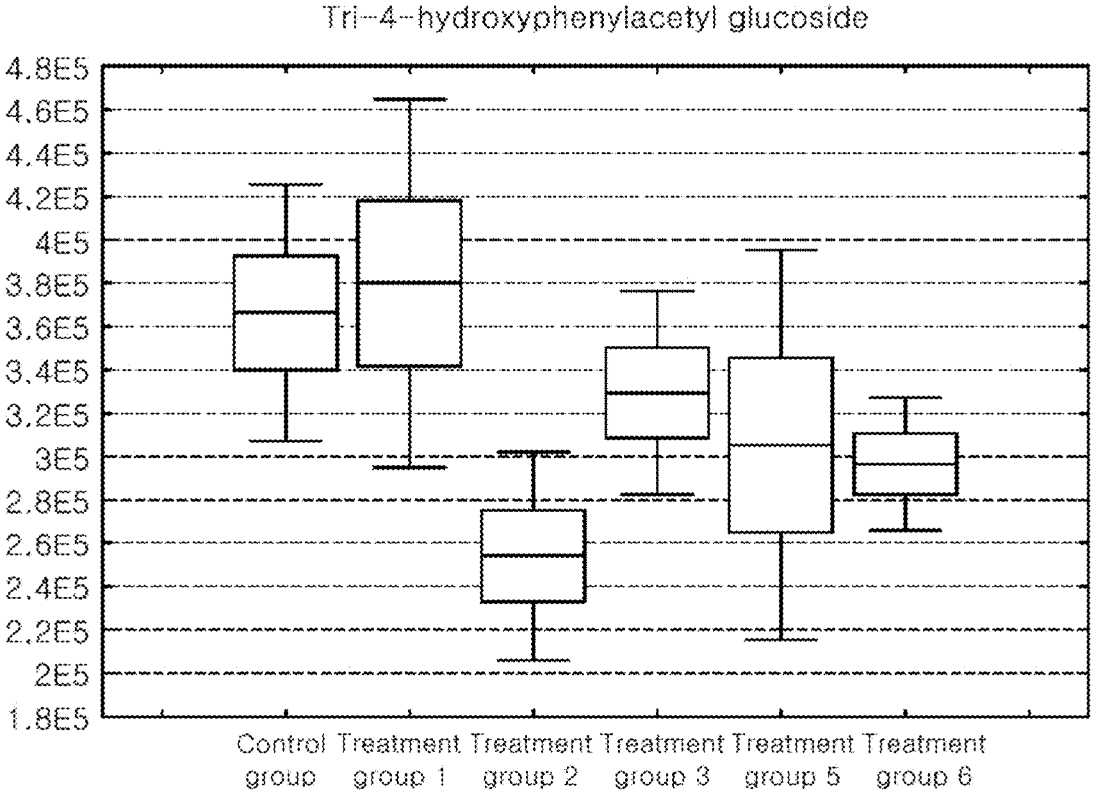

FIG. 35 to FIG. 37 are graphs depicting analysis results of sesquiterpene lactone-based metabolites and other metabolites according to conditions on day 8 under UV treatment.

Referring to FIG. 35 to FIG. 37, the contents of lactucopicrin-15-oxalate, lactucopicrin and tri-4-hydroxyphenylacetyl glucoside in all of the treatment groups were similar to or smaller than the contents thereof in the control group.

However, the contents of lactucopicrin-15-oxalate and lactucopicrin were similar in the treatment groups irradiated with UVB, that is, in Treatment group 1, Treatment group 2, Treatment group 3 and Treatment group 6 to the contents thereof in the control group and were much smaller in the treatment group irradiated with UVA, that is, in Treatment group 5, than in the control group.

In addition, Treatment group 2 had a much smaller content of tri-4-hydroxyphenylacetylglucoside than the control group.

It could be seen that both UVA and UVB increased the contents of hydroxycinnamic acid-based metabolites, anthocyanin-based metabolites, and flavonoid-based luteolin hydroxymalonyl hexoside through change of the second metabolites on day 8 under UV treatment.

Light having a peak wavelength of 295 nm and an intensity of 0.1 W increased the contents of luteolin hydroxymalonyl hexoside and quercetin-3-O-malonylglucoside among flavonoid-based metabolites.

Light having a peak wavelength of 295 nm and an intensity of 0.3 W generally increased the content of hydroxycinnamic acid-based metabolites.

UVA increased the contents of quercetin-3-O-(6"-O-malonyl)-glucoside-7-O-glucoside and kaempferol malonyl glucoside among the flavonoid-based metabolites more than UVB.

Light having a peak wavelength of 295 nm and an intensity of 0.3 W significantly decreased the content of flavonoid-based metabolites excluding luteolin hydroxymalonyl hexoside.

Further, UVA significantly decreased the content of sesquiterpene lactone-based lactucopicrin.

As such, UVA and UVB may have different effects depending upon the kind of phytochemical. That is, the kind of metabolites in a plant differs depending upon the wavelength and intensity of light. Accordingly, the content of phytochemicals in a plant may be adjusted depending upon the kind of phytochemical and the type of light.

Figure 38:
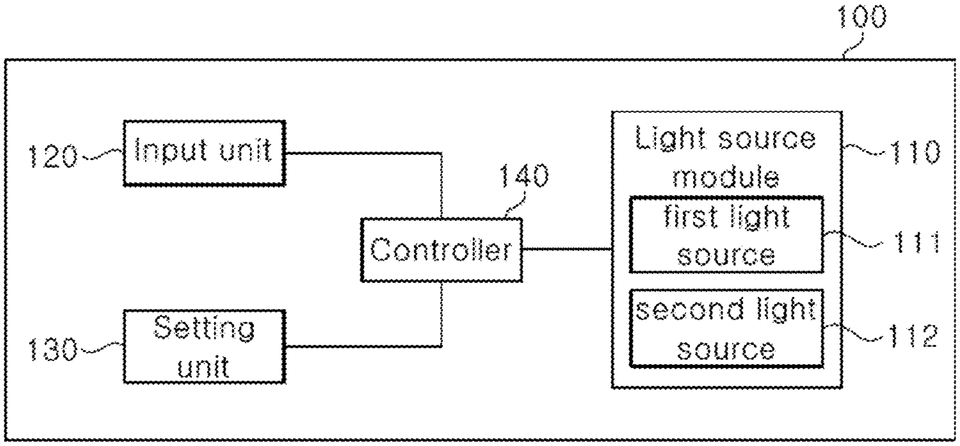
FIG. 38 is a block diagram of a light source module for plant cultivation according to one embodiment of the present disclosure.

FIG. 38 is a block diagram of a light source module for plant cultivation according to one embodiment of the present disclosure.

Referring to FIG. 38, a light source device 100 for plant cultivation may include a light source module 110, an input unit 120, a setting unit 130, and a controller 140. Here, the light source module 110 is a light source module for plant cultivation adapted to emit light towards plants.

The light source module 110 includes a first light source 111 and a second light source 112.

The first light source 111 and the second light source 112 may emit light having different peak wavelengths.

For example, the first light source 111 may emit UVB and the second light source 112 may emit UVA. In addition, the first light source 111 may emit light having a peak wavelength of 295 nm and the second light source 112 may emit light having a peak wavelength of 385 nm.

Each of the first light source 111 and the second light source 112 may include a light emitting diode. Since the light emitting diode has a smaller half-width than a lamp, the light emitting diode facilitates selective irradiation of a plant with light having a desired wavelength band. For example, the first light source 111 and the second light source 112 may have a half-width of 30 nm or less.

The first light source 111 and the second light source 112 may be individually operated. Accordingly, either one of the first light source 111 and the second light source 112 or both of the first light source 111 and the second light source 112 may be operated at the same time.

Since the first light source 111 and the second light source 112 are individually operated, plants can be supplied with light in various wavelength bands in various ways.

The input unit 120 receives an external signal for controlling operation of the light source device 100.

For example, it is possible to select the kind of phytochemical to be increased in content in the plants through the input unit 120.

In addition, it is possible to select the type of light for UV treatment, light intensity, a light treatment time, an irradiation method, and the like through the input unit 120.

The setting unit 130 may previously store various data for UV treatment for increase in phytochemical content depending upon the kind of phytochemical.

The setting unit 130 may set the UV treatment method in response to the external signal received from the input unit 120 based on the data previously stored therein.

For example, the setting unit 130 may set the type of light for UV treatment, the light intensity, the light treatment time, and the irradiation method corresponding to a selected kind of phytochemical through the data previously stored therein.

The controller 140 may control operation of the light source module 110 depending upon the UV treatment method selected through the input unit 120.

For example, the controller 140 may supply electric power to at least one of the first light source 111 and the second light source 112 to emit light depending upon the type of light selected through the input unit 120. Here, the controller 140 may supply electric power to the light source module 110 for a light treatment time selected through the input unit 120. In addition, the electric power may be supplied from an external power source outside the light source device 100 or an internal power source therein.

The controller 140 may control the intensity of light emitted from the first light source 111 and the second light source 112 by adjusting the magnitude of electric power supplied to the first light source 111 and the second light source 112 depending upon the intensity of light selected through the input unit 120.

Further, the controller 140 may control the first light source 111 and the second light source 112 to continuously emit light or to repeat emission of light and stopping emission of the first type of light depending upon the irradiation method selected through the input unit 120.

The controller 140 may control the light source module 110 in response to the received signal. That is, the controller 140 may allow or stop power supply to the first light source 111 and the second light source 112 depending upon the irradiation method selected through the input unit 120. Here, power may be supplied from an external power source outside the light source device 100 or an internal power source therein.

Further, the controller 140 may control the intensity of light emitted from the first light source 111 and the second light source 112 through control of power supply thereto depending upon the irradiation method selected through the input unit 120.

Further, the controller 140 may control the light source module 110 depending upon the irradiation method set on the input unit 120. The controller 140 allows power supply to the light source module 110 in response to a signal including data with respect to the UV treatment method received from the setting unit 130 such that a plant can be subjected to UV treatment by the UV treatment method. According to this embodiment, the light source device 100 can selectively increase a particular phytochemical content among phytochemicals in the plant by irradiating the plant with light in various wavelength bands in various ways.

Although the light source device 100 is described as including the first light source 111 and the second light source 112 in this embodiment, it should be understood that other implementations are also possible. The light source device 100 may further include a light source emitting visible light as well as the light source for emitting UV light. Further, the light source device 100 may further include a light source emitting UV light having a different peak wavelength than the first light source 111 and the second light source 112.

Although some embodiments have been described herein in conjunction with the accompanying drawings, it should be understood that these embodiments are provided for illustration only and are not to be construed in any way as limiting the present disclosure. The scope of the present disclosure should be defined by the appended claims and equivalents thereto.

The invention claimed is:

1. A light source module for plant cultivation adapted to change a phytochemical content in a plant through UV treatment of the plant, the light source module comprising:

a first light source configured to emit a first type of light for changing a content of at least one phytochemical of multiple phytochemicals; and a second light source configured to emit a second type of light that changes a content of at least one different kind of other phytochemical of the multiple phytochemicals, wherein the first light source and the second light source are individually operated;

the first type of light and the second type of light are ultraviolet (UV) light having different peak wavelengths;

at least one of the first type of light or the second type of light is UVB; and the first light source emits the first type of light for 6 hours in a daily photoperiod.

2. The light source module for plant cultivation according to claim 1, wherein the first type of light is UVB and the second type of light is UVA.

3. The light source module for plant cultivation according to claim 2, wherein the light source module increases a content of at least one of: hydroxycinnamic acid, flavonoids, or anthocyanin, in the plant through UV treatment.

4. The light source module for plant cultivation according to claim 2, wherein the second type of light is UV light having a peak wavelength of 385 nm.

5. The light source module for plant cultivation according to claim 4, wherein the second type of light has an irradiance of 30 $W/m^2$.

6. The light source module for plant cultivation according to claim 4, wherein the second type of light increases a content of at least one of: hydroxycinnamic acid-based caffeoyltartaric acid, flavonoid-based quercetin-3-O-(6"-O-malonyl)-glucoside-7-O-glucoside, or kaempferol malonyl glucoside.

7. The light source module for plant cultivation according to claim 2, wherein the second light source continuously emits the second type of light for a period of UV treatment.

8. The light source module for plant cultivation according to claim 1, wherein the first type of light is UV light having a peak wavelength of 295 nm.

9. The light source module for plant cultivation according to claim 8, wherein the first type of light has an irradiance of 0.1 $W/m^2$ or 0.3 $W/m^2$.

10. The light source module for plant cultivation according to claim 8, wherein the first type of light increases a content of at least one of: hydroxycinnamic acid, anthocyanin, flavonoid-based quercetin-3-O-malonyl glucoside, or luteolin hydroxymalonyl hexoside.

11. The light source module for plant cultivation according to claim 1, wherein the first light source continuously emits the first type of light.

12. The light source module for plant cultivation according to claim 1, wherein the first light source repeats emission of the first type of light and stopping emission of the first type of light.

13. The light source module for plant cultivation according to claim 1, wherein UV treatment is performed for 4 to 8 days.

14. A light source device for plant cultivation comprising:
- a light source module for performing UV treatment on a plant by irradiating the plant with UV light;
- an input unit that receives an external signal having a selection;
- a setting unit that sets a UV treatment method based on the selection in response to the external signal from the input unit; and
- a controller that is configured to supply electric power from an external power source to the light source module in accordance with the selection in response to a signal from the input unit or the setting unit,
- the light source module comprising:
  - a first light source configured to emit a first type of light for changing a content of at least one phytochemical of multiple phytochemicals; and
  - a second light source configured to emit a second type of light for changing a content of at least one other different kind of phytochemical of multiple phytochemicals,
- wherein
  - the first light source and the second light source are individually operated; and
  - the first type of light and the second type of light are ultraviolet (UV) light having different peak wavelengths;
  - at least one of the first type of light or the second type of light is UVB; and
  - the first light source emits the first type of light for 6 hours in a daily photoperiod.

15. The light source device for plant cultivation according to claim 14, wherein at least one of the first type of light or the second type of light is UVB.

16. The light source device for plant cultivation according to claim 15, wherein the first type of light is UV light having a peak wavelength of 295 nm.

17. The light source device for plant cultivation according to claim 16, wherein the controller controls the first light source to emit the first type of light at an irradiance of 0.1 $W/m^2$ or 0.3 $W/m^2$.

18. The light source device for plant cultivation according to claim 16, wherein the first type of light increases a content of at least one of: hydroxycinnamic acid, anthocyanin, or flavonoid-based quercetin-3-O-malonyl glucoside and luteolin hydroxymalonyl hexoside.

19. The light source device for plant cultivation according to claim 15, wherein the controller controls the first light source to emit the first type of light for 6 hours in a daily photoperiod.

20. The light source device for plant cultivation according to claim 19, wherein the controller controls the first light source to repeat emission of the first type of light and stopping emission of the first type of light.

21. The light source device for plant cultivation according to claim 15, wherein the controller controls the first light source to continuously emit the first type of light.

22. The light source device for plant cultivation according to claim 14, wherein the first type of light is UVB and the second type of light is UVA.

23. The light source device for plant cultivation according to claim 22, wherein the light source device increases the content of at least one of: hydroxycinnamic acid, flavonoids, or anthocyanin, in the plant through UV treatment.

24. The light source device for plant cultivation according to claim 22, wherein the second type of light is UV light having a peak wavelength of 385 nm.

25. The light source device for plant cultivation according to claim 24, wherein the controller controls the second light source to emit the second type of light at an irradiance of 30 $W/m^2$.

26. The light source device for plant cultivation according to claim 24, wherein the second type of light increases the content of at least one of: hydroxycinnamic acid-based caffeoyltartaric acid, flavonoid-based quercetin-3-O-(6"-O-malonyl)-glucoside-7-O-glucoside, or kaempferol malonyl glucoside.

27. The light source device for plant cultivation according to claim 22, wherein the controller controls the second light source to continuously emit the second type of light for a period of UV treatment.

28. The light source device for plant cultivation according to claim 14, wherein UV treatment is performed for 4 to 8 days.

29. The light source device for plant cultivation according to claim 14, wherein the selection comprises one selected from among: a kind of phytochemical, the type of light, light intensity, a light treatment time, and an irradiation method.

30. The light source device for plant cultivation according to claim 29, wherein:

the setting unit sets a UV treatment method based upon the kind of phytochemical selected in the selection received by the input unit; and the controller controls the light source module in response to a signal including data of the UV treatment method received from the setting unit, the UV treatment method including at least one of: the type of light, the light intensity, the light treatment time, or the irradiation method.

31. A light source module for plant cultivation adapted to change a phytochemical content in a plant through UV treatment of the plant, the light source module comprising:

a first light source configured to emit a first type of light for changing a content of at least one phytochemical of multiple phytochemicals; and a second light source configured to emit a second type of light that changes a content of at least one different kind of other phytochemical of the multiple phytochemicals, wherein the first light source and the second light source are individually operated;

the first type of light and the second type of light are ultraviolet (UV) light having different peak wavelengths; and the first type of light is UV light has a peak wavelength of 295 nm and an irradiance of 0.1 $W/m^2$ or 0.3 $W/m^2$.

32. The light source module for plant cultivation according to claim 31, wherein the first type of light increases a content of at least one of: hydroxycinnamic acid, anthocyanin, flavonoid-based quercetin-3-O-malonyl glucoside, or luteolin hydroxymalonyl hexoside.

* * * * *